(12) United States Patent
Rosenman et al.

(10) Patent No.: US 12,333,729 B2
(45) Date of Patent: Jun. 17, 2025

(54) AUTOMATIC STAGING OF NON-SMALL CELL LUNG CANCER FROM MEDICAL IMAGING AND BIOPSY REPORTS

(71) Applicant: Siemens Medical Solutions USA, Inc., Malvern, PA (US)

(72) Inventors: Julian Rosenman, Chapel Hill, NC (US); Zhoubing Xu, Plainsboro, NJ (US); Ali Kamen, Skillman, NJ (US); Fernando Vega, Erlangen (DE); Nicolo Capobianco, Erlangen (DE); Bruce Spottiswoode, Knoxville, TN (US); Sasa Grbic, Plainsboro, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 450 days.

(21) Appl. No.: 17/819,256

(22) Filed: Aug. 11, 2022

(65) Prior Publication Data
US 2024/0054650 A1    Feb. 15, 2024

(51) Int. Cl.
*G06T 7/00*    (2017.01)
*G16H 10/60*    (2018.01)
(Continued)

(52) U.S. Cl.
CPC .......... *G06T 7/0016* (2013.01); *G16H 10/60* (2018.01); *G16H 30/40* (2018.01); *G16H 50/20* (2018.01);
(Continued)

(58) Field of Classification Search
CPC ......... G06T 7/0016; G06T 2207/20081; G06T 2207/30061; G06T 2207/30096;
(Continued)

(56) References Cited

U.S. PATENT DOCUMENTS

| 2009/0215042 A1* | 8/2009 | Sella-Tavor | ......... | C12Q 1/6886 |
| | | | | 435/7.1 |
| 2020/0085382 A1* | 3/2020 | Taerum | ................ | A61B 5/7264 |

(Continued)

OTHER PUBLICATIONS

Detterbeck et al., "The eighth edition TNM stage classification for lung cancer: What does it mean on main street?", The Journal of Thoracic and Cardiovascular Surgery, 2018, pp. 356-359.
(Continued)

*Primary Examiner* — Iriana Cruz

(57) ABSTRACT

Systems and methods for automatically staging non-small cell lung cancer are provided. Patient data relating to a cancer of a patient is received. The patient data comprises one or more medical images and one or more biopsy reports. A T-stage of the cancer is determined based on a location and a size of one or more tumors of the cancer determined using the patient data. An N-stage of the cancer is determined by combining a metastasis evaluation of the cancer to regional lymph nodes determined from the one or more medical images and a metastasis evaluation of the cancer in the regional lymph nodes determined from the one or more biopsy reports. An M-stage of the cancer is determined based on a metastasis evaluation of the cancer to anatomical structures based on the patient data. The T-stage, the N-stage, and the M-stage are output.

20 Claims, 15 Drawing Sheets

(51) Int. Cl.
  *G16H 30/40* (2018.01)
  *G16H 50/20* (2018.01)
(52) U.S. Cl.
  CPC ............... *G06T 2207/20081* (2013.01); *G06T 2207/30061* (2013.01); *G06T 2207/30096* (2013.01)
(58) Field of Classification Search
  CPC . G06T 2207/10081; G06T 2207/10104; G06T 2207/20084; G06T 7/0012; G16H 10/60; G16H 30/40; G16H 50/20; G16H 50/30
  See application file for complete search history.

(56) References Cited

U.S. PATENT DOCUMENTS

| | | | | |
|---|---|---|---|---|
| 2021/0090694 | A1* | 3/2021 | Colley | G16B 30/00 |
| 2023/0196561 | A1* | 6/2023 | Choi | G06T 7/11 |
| | | | | 382/128 |
| 2024/0005502 | A1* | 1/2024 | Washko, Jr. | G06T 7/0014 |
| 2024/0242835 | A1* | 7/2024 | Giltnane | G06T 7/0012 |
| 2024/0395407 | A1* | 11/2024 | Esteva | G16H 10/40 |

OTHER PUBLICATIONS

Feng et al., "The new 8th TNM staging system of lung cancer and its potential imaging interpretation pitfalls and limitations with CT image demonstrations", Diagnostic and Interventional Radiology, 2019, pp. 270-279.
Warner et al., "Feasibility and Accuracy of Extracting Cancer Stage Information From Narrative Electronic Health Record Data", Journal of Oncology, 2016, pp. 157-158.
Available at: https://www.nccn.org/professionals/physician_gls/pdf/nscl.pdf (National Comprehensive Cancer Network login and password needed); 2022.
Kligerman et al., "Staging of non-small cell lung cancer using integrated PET/CT", American Journal Roentgenology, 2009, pp. 1203-1211.
Yasufuku et al., "Comparison of endobronchial ultrasound, positron emission tomography, and CT for lymph node staging of lung cancer", Chest Journal, 2006, pp. 710-708.
McNally et al., "Mediastinoscopy", StatPearls, NCBI Bookshelf, National Library of Medicine, National Institutes of Health, 2021, 6 pgs.
Garapati et al., "Urinary bladder cancer staging in CT urography using machine learning", Medical Physics, 2017, 10 ogs.
Moitra et al., "Automated AJCC (7th edition) staging of non-small cell lung cancer (NSCLC) using deep convolutional neural network (CNN) and recurrent neural network (RNN)", Health Information Science and Systems, 2019, 12 pgs.
Ardila et al., "End-to-end lung cancer screening with three-dimensional deep learning on low-dose chest computed tomography", Natural Medicine, 2019, 25 pgs.
Kunstman et al., "Artificial Intelligence in Cancer Staging: Limitless Potential or Passing Fad?", Annals Surgical Oncology, 2020, pp. 978-979.
Capobianco et al., "Whole-body uptake classification and prostate cancer staging in 68Ga-PSMA-11 PET/CT using dual-tracer learning", European Journal Nuclear Medicine Molecular Imaging, 2021, pp. 517-526.
Chamberlin et al., "Automated detection of lung nodules and coronary artery calcium using artificial intelligence on low-dose CT scans for lung cancer screening: accuracy and prognostic value", 2021, BMC Medicine, 14 pgs.
Fischer et al., "Artificial Intelligence-based Fully Automated Per Lobe Segmentation and Emphysema-quantification Based on Chest Computed Tomography Compared With Global Initiative for Chronic Obstructive Lung Disease Severity of Smokers", Journal of Thorac Imaging, 2020, pp. S28-S34.
Hu et al., "Automatic Extraction of Lung Cancer Staging Information From Computed Tomography Reports: Deep Learning Approach", JMIR Medical Informatics, 2021, 17 pgs.
"Endobronchial Ultrasound (EBUS) Bronchoscopy Procedure", Temecula Valley Hospital, https://www.temeculavalleyhospital.com/services/oncology/ebus, 2022, 4 pgs.
Sibille et al., "18F-FDG PET/CT Uptake Classification in Lymphoma and Lung Cancer by Using Deep Convolutional Neural Networks", Radiology, 2020, 8 pgs.
Kay et al., "Revisions to the Tumor, Node, Metastasis staging of lung cancer (8th edition): Rationale, radiologic findings and clinical implications", World Journal of Radiology, 2017, pp. 269-279.
Aquino et al., "Nerves of the thorax: atlas of normal and pathologic findings", Radiographics, 2001, pp. 1275-1281.
El-Sherief et al., "International association for the study of lung cancer (IASLC) lymph node map: radiologic review with CT illustration", Radiographics, 2014 pp. 1680-1691.
Thulkar et al., "Multimodality Staging of Lung Cancer", PET Clin, 2011, pp. 251-263.
UyBico et al., "Lung cancer staging essentials: the new TNM staging system and potential imaging pitfalls", Radiographics, 2010, pp. 1163-1181.
Seifert et al., "Semiautomatically quantified tumor vol. using 68Ga-PSMA-11 PET as a biomarker for survival in patients with advanced prostate cancer", Journal of Nuclear Medicine, 2020, pp. 1786-1792.
Yang et al., "Automatic liver segmentation using an adversarial image-to-image network", Springer International Publishing, 2017, pp. 507-515.
Kratzke et al., "DirectORGANS 2.0 White Paper—The world's first contours generated by a CT simulator—Technical principles and clinical evaluation", Siemens-Healthineers.com/radiotherapy, 2021, 16 pgs.
Wikipedia, "Recurrent Laryngeal Nerve", https://en.wikipedia.org/wiki/Recurrent_Laryngeal_Nerve, 2022, 9 pgs.
Smithuis, "Mediastinal Lymph Node Map", Radiology Assistant, 2009, 20 pgs.
"Surgery for Lung Cancer"—Patient Education, Fairview, https://www.fairview.org/patient-education/82996, 2022, 4 pgs.
Call et al., "Cervical mediastinoscopy and video-assisted mediastinoscopic lymphadenectomy for the staging of non-small cell lung cancer", Mediastinum, 2019, pp. 1-7.

* cited by examiner

| Number | Name | Description | |
|---|---|---|---|
| | Tumor-Centered Tools | | |
| ① | Tumor detector | Identifies tumors and tumor nodules of all sizes | 302-A |
| ② | Tumor classifier | Determines likelihood of tumors being benign or malignant | 302-B |
| ③ | Tumor size | Measure the primary tumor size along the longer axis | 302-C |
| ④ | Tumor T, N, or M? | Classifies a tumor as primary, hilar, mediastinal, or metastatic | 302-D |
| ⑤ | Primary tumor locater | Determines the location of the primary tumor (e.g., which lobe) | 302-E |
| ⑥ | Tumor location by anatomy | Outputs adjacent anatomy | 302-F |
| | Anatomy-Centered Tools | | |
| ⑦ | Anatomy identifier | Annotates lobes of the lung and other key anatomy | 304-A |
| ⑧ | Pneumonitis/effusions/ atelectasis | Detects and classifies these three abnormalities | 304-B |
| | Text Manipulation Tools | | |
| ⑨ | Manual input | Allows user to input various critical decisions in the form of objective questions. | 306-A |
| ⑩ | Text input | Reads and interprets text for use in critical decision making | 306-B |
| ⑪ | Text-to-image | Reads text reports of tumor locations and anatomic locations and displays that information on CT scans | 306-C |
| | Lymph Node Station Identifier | | |
| ⑫ | Lymph node annotator | Identifies the lymph node stations of the hilum and mediastinum | 308-A |

Columns labeled: 310 (Number), 312 (Name), 314 (Description)

Groups: 302 (Tumor-Centered Tools), 304 (Anatomy-Centered Tools), 306 (Text Manipulation Tools), 308 (Lymph Node Station Identifier)

AUTOMATIC STAGING OF NON-SMALL CELL LUNG CANCER FROM MEDICAL IMAGING AND BIOPSY REPORTS

TECHNICAL FIELD

The present invention relates generally to automatic staging of cancer, and in particular to automatic staging of non-small cell lung cancer from medical imaging and biopsy reports.

BACKGROUND

Cancer staging is the process of determining the extent to which cancer has grown and spread in a patient. Clinical staging of non-small cell lung cancer is based entirely on information obtained before the initial treatment using patient data such as patient history, physical examination, laboratory studies, medical imaging, and biopsies. For non-small cell lung cancer, a patient's clinical stage consists of three separate components: the T-stage representing the status of the primary tumor, the N-stage representing the metastasis of the cancer to regional lymph nodes, and the M stage representing the metastasis of the cancer to other anatomical structures and organs. Each of these components is divided into several distinct categories: T1 through T4, N0 though N3, and M0 or M1. In addition, each of these categories may contain subcategories, such as T1 a, for example. The rules for specifically staging non-small cell lung cancer are detailed, complex, and often require careful radiographic measurements and subjective judgments. Not only is this process time consuming, but it has shown that it can often lead to conflicting results when performed by different physicians.

BRIEF SUMMARY OF THE INVENTION

In accordance with one or more embodiments, systems and methods for automatically staging non-small cell lung cancer are provided. Patient data relating to a cancer of a patient is received. The patient data comprises one or more medical images and one or more biopsy reports. A T-stage of the cancer is determined based on a location and a size of one or more tumors of the cancer determined using the patient data. An N-stage of the cancer is determined by combining a metastasis evaluation of the cancer in regional lymph nodes determined from the one or more medical images and a metastasis evaluation of the cancer in the regional lymph nodes determined from the one or more biopsy reports. An M-stage of the cancer is determined based on a metastasis evaluation of the cancer in anatomical structures based on the patient data. The T-stage, the N-stage, and the M-stage are output.

In one embodiment, the N-stage is determined by comparing the metastasis evaluation of the cancer in the regional lymph nodes determined from the one or more medical images and the metastasis evaluation of the cancer in the regional lymph nodes determined from the one or more biopsy reports. Combined metastasis results are determined based on the comparing. The N-stage of the cancer is determined based on the combined metastasis results. In one embodiment, the metastasis evaluation of the cancer in the regional lymph nodes determined from the one or more medical images and the metastasis evaluation of the cancer in the regional lymph nodes determined from the one or more biopsy reports are compared based on a level of evidence. The level of evidence comprises 1) a first level of evidence comprising a positive biopsy result, 2) a second level of evidence comprising negative metastasis regions determined from the one or more medical images, 3) a third level of evidence comprising a negative biopsy result, and 4) a fourth level of evidence comprising positive metastasis regions determined from the one or more medical images.

In one embodiment, the one or more tumors is determined to be located in an area around a phrenic nerve in response to a diaphragm of the patient being at least partially paralyzed. The T-stage of the cancer is determined based on the determination that the one or more tumors are located in the area around the phrenic nerve.

In one embodiment, it is determined whether a detection and a malignancy classification of the one or more tumors determined from the one or more medical images conform to the one or more biopsy reports.

In one embodiment, a path taken along a series of decisions for the determining the T-stage, the determining the N-stage, and the determining the M-stage is presented.

In one embodiment, the determining the T-stage, the determining the N-stage, and the determining the M-stage are performed using one or more machine learning based networks.

In one embodiment, the cancer is a non-small cell lung cancer.

These and other advantages of the invention will be apparent to those of ordinary skill in the art by reference to the following detailed description and the accompanying drawings.

BRIEF DESCRIPTION OF THE DRAWINGS

FIG. 3 shows a table of tools utilized for automatic staging of cancer, in accordance with one or more embodiments;

DETAILED DESCRIPTION

The present invention generally relates to methods and systems for automatic staging of non-small cell lung cancer from medical imaging and biopsy reports. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for a deep machine learning AI (artificial intelligence) based system for clinical use for automatically and reliably staging non-small cell lung cancer using patient data such as, e.g., medical images, biopsy reports, and/or clinical data of the patient. The deep machine learning AI based system stages the patient according to the TNM staging system, where T represents the size of the original (primary) tumor and the extent that it has invaded nearby tissue, N represents the extent that the primary tumor has invaded nearby (regional) lymph nodes, and M represents distant metastasis (spread of cancer from one part of the body to another). Advantageously, embodiments described herein ensure that 1) all patients are properly staged, limited only by the amount and quality of the input data, 2) staging inconsistencies between different physicians avoided, and 3) considerable amounts of time and effort for manually staging the patient are potentially saved.

Figure 1:
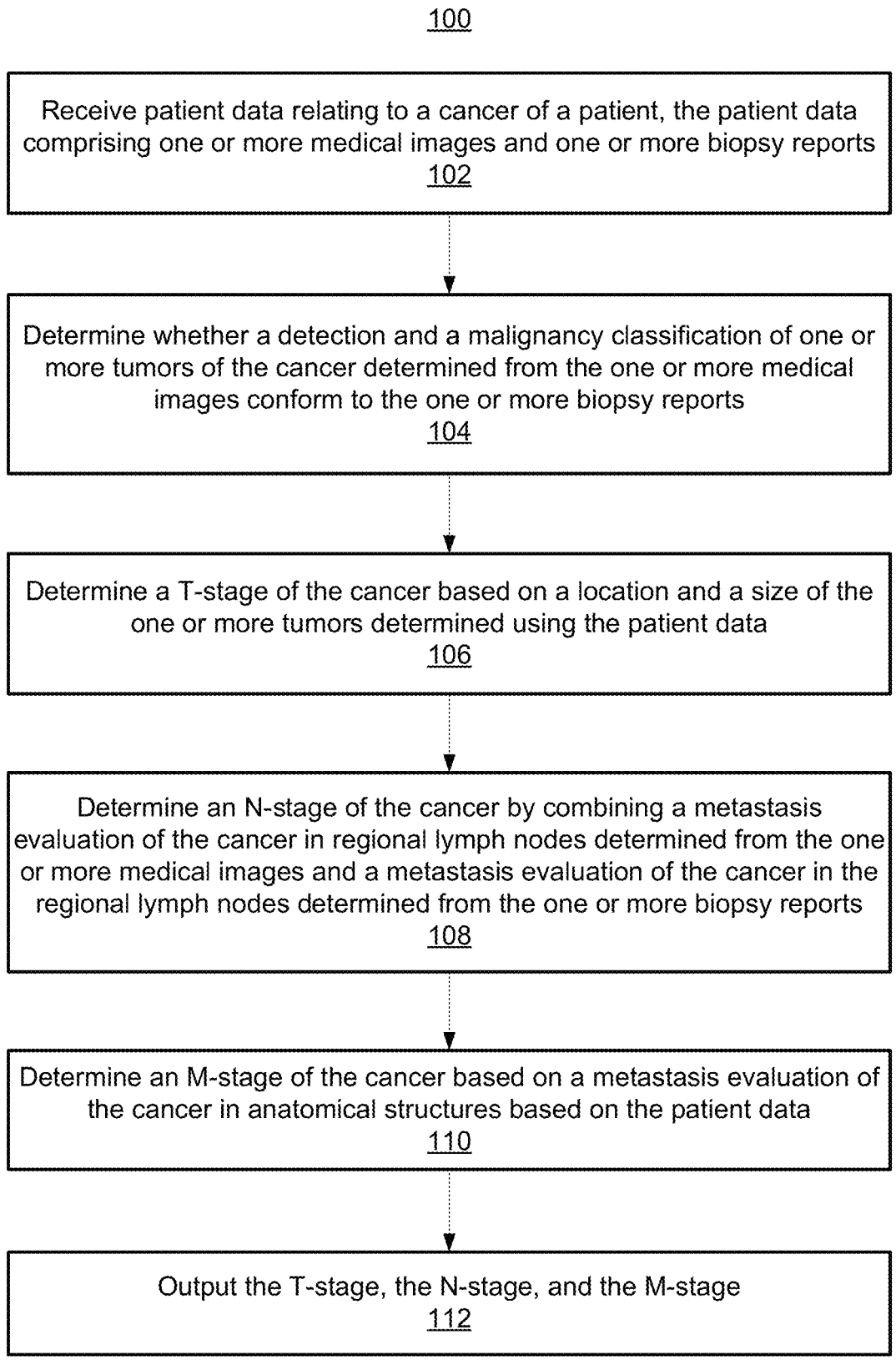
FIG. 1 shows a method for automatic staging of cancer, in accordance with one or more embodiments.
Figure 2:
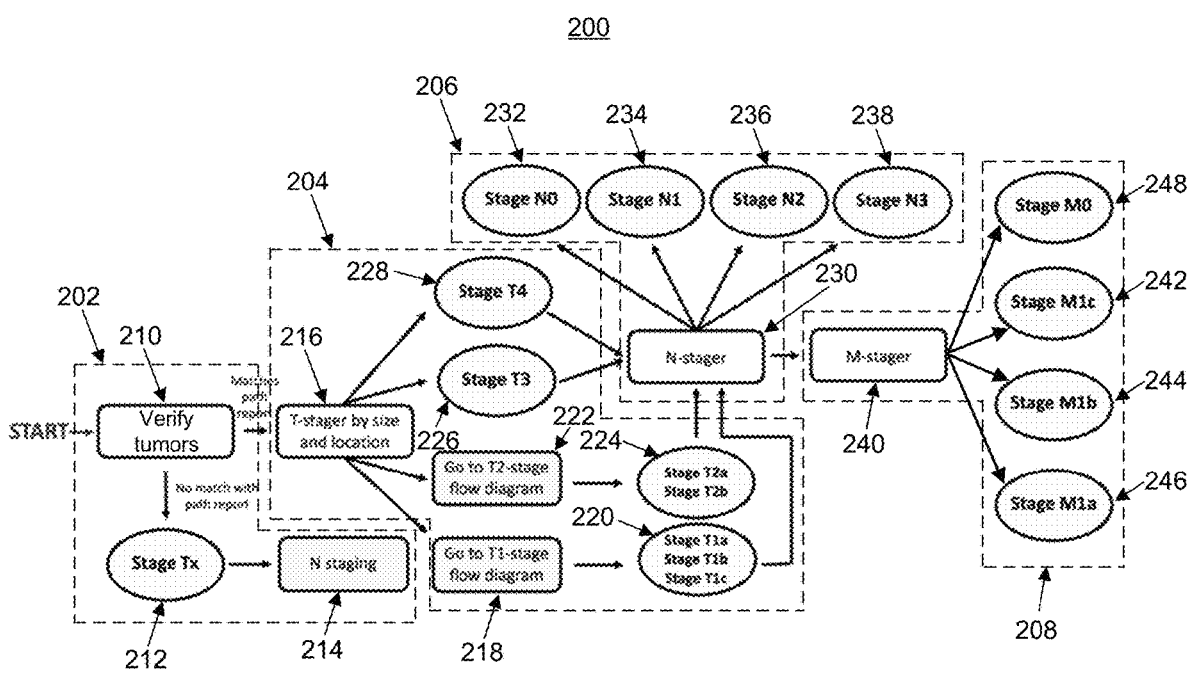
FIG. 2 shows a workflow for automatic staging of cancer, in accordance with one or more embodiments.

FIG. 1 shows a method 100 for automatic staging of cancer, in accordance with one or more embodiments. The steps of method 100 may be performed by one or more suitable computing devices, such as, e.g., computer 1502 of FIG. 15. FIG. 2 shows a workflow 200 for automatic staging of cancer, in accordance with one or more embodiments. FIG. 1 and FIG. 2 will be described together. One or more steps of method 100 of FIG. 1 (e.g., steps 104, 106, 108, and/or 110) and workflow 200 of FIG. 2 may be performed utilizing one or more tools identified FIG. 3.

FIG. 3 shows a table 300 of tools utilized for automatic staging of cancer, in accordance with one or more embodiments. Such tools comprise tumor-centered tools 302, anatomy-centered tools 304, text manipulation tools 306, and lymph node station identifier tools 308. Tumor-centered tools 302 comprise tumor detector tool 302-A, tumor classifier tool 302-B, tumor size tool 302-C, tumor T, N, or M tool 302-D, primary tumor locator tool 302-E, and tumor location by anatomy tool 302-F. Tumor location by anatomy tool 302-F outputs adjacent anatomies (e.g., diaphragm, mediastinum, heart, great vessels, trachea, bronchi, recurrent laryngeal nerve, esophagus, vertebral body, carina, pleura wall, chest wall, or phrenic nerve). Anatomy-centered tools 304 comprise anatomy identifier tool 304-A and pneumonitis/effusions/atelectasis detector and classifier tool 304-B. Text manipulation tools 306 comprise manual input tool 306-A, text input tool 306-B, and text-to-image tool 206-C. Lymph node station identifier 308 comprises lymph node annotator tool 308-A. The tools identified in table 300 may be implemented using one or more machine learning based networks. Table 300 comprises column 310 assigning an identification number to identify the utilization tools throughout the figures, column 312 representing a name of the tools, and column 314 representing a description of the tools.

At step 102 of FIG. 1, patient data relating to a cancer of a patient is received. The patient data may comprise any suitable data relating to the cancer of the patient. In one embodiment, the cancer comprises lung cancer, such as, e.g., non-small cell lung cancer. However, the cancer may be any other suitable cancer of the patient.

In one embodiment, the patient data may comprise one or more medical images of the patient. The one or more medical images may be of any suitable modality. For example, in one embodiment, the one or more medical images are CT (computed tomography) images acquired with or without a contrast agent. In another embodiment, the one or more medical images are PET/CT (positron emission tomography/CT) images. The PET/CT images may be supplemented with EBUS-TBNA (endobronchial ultrasound transbronchial needle aspirations) or MED (mediastinoscopy with biopsy). However, the one or more medical images may be of any other suitable modality, such as, e.g., MRI (magnetic resonance imaging), ultrasound, x-ray, or any other medical imaging modality or combinations of medical imaging modalities. The one or more medical images may be 2D (two dimensional) images and/or 3D (three dimensional) volumes, and may comprise a single medical image or a plurality of medical images.

In one embodiment, the patient data may comprise one or more biopsy reports of tumors of the patient. The one or more biopsy reports comprise results of biopsies performed on the tumors identifying a location of the one or more tumors and a malignancy classification of the tumors (as being malignant or benign).

In one embodiment, the patient data may comprise clinical information of the patient. The clinical information of the patient may comprise any clinical information of the patient, such as, e.g., patient medical history, patient demographic information, laboratory results, etc.

The patient data may be received by loading the patient data from a storage or memory of a computer system or receiving the patient data from a remote computer system. Where the patient data comprises one or more input medical images, the one or more input medical images may be received directly from an image acquisition device, such as, e.g., a CT scanner, as the medical images are acquired.

At step 104 of FIG. 1, it is determined whether a detection and a malignancy classification of one or more tumors of the cancer determined from the one or more medical images conform to the one or more biopsy reports.

In one example, as shown in FIG. 2, it is determined whether the detection and the classification conform to the one or more biopsy reports at stage 202 of workflow 200. At step 210, the detection and malignancy classification of one or more primary tumors of the cancer is verified with one or more biopsy reports. If the detection and the malignancy classification conform to the biopsy reports, workflow 200 proceeds to stage 204. If the detection and the classification do not conform to the biopsy reports, workflow 200 proceeds to step 212 and a T-stage of Tx is assigned, indicating that the one or more primary tumors cannot be assessed. Workflow 200 proceeds to N staging at step 214, which is performed at stage 206. Stage 202 of workflow 200 is described in further detail below with respect to FIG. 4.

Figure 4:
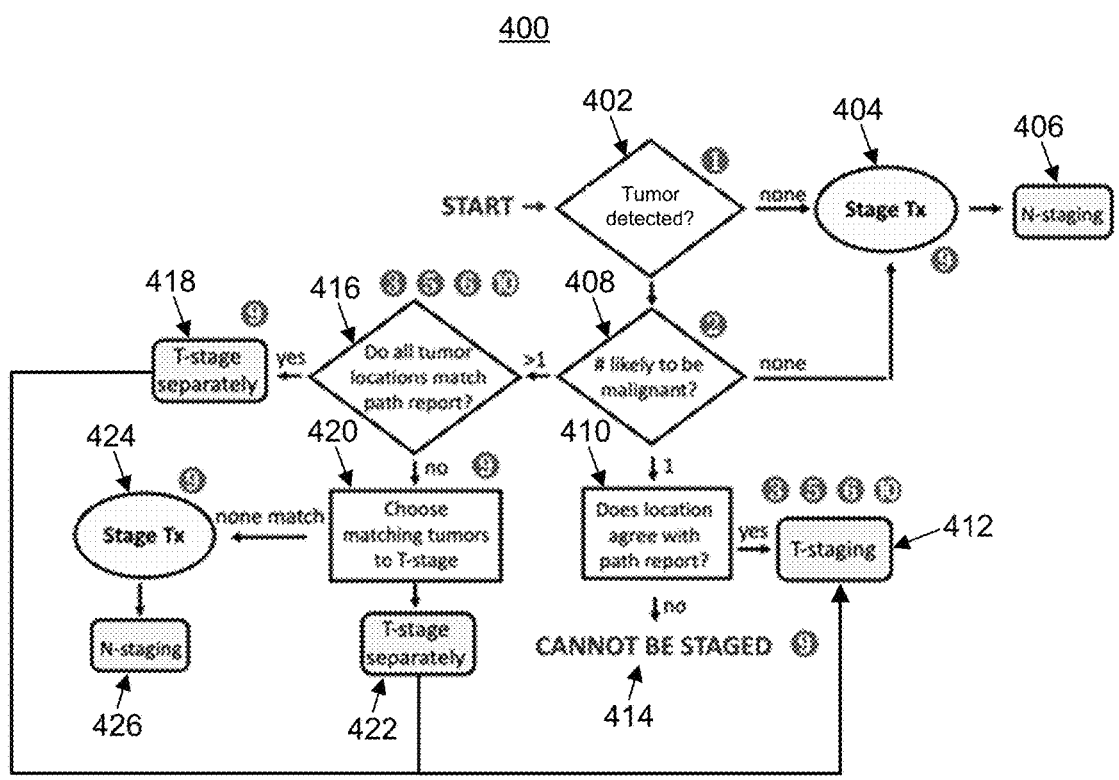
FIG. 4 shows a workflow for determining whether a detection and a malignancy classification of one or more tumors of a cancer conform to one or more biopsy reports, in accordance with one or more embodiments.

FIG. 4 shows a workflow 400 for determining whether a detection and a malignancy classification of one or more tumors of a cancer conform to one or more biopsy reports, in accordance with one or more embodiments. Workflow 400 may be performed at step 104 of FIG. 1 or step 210 of FIG. 2. Certain steps of workflow 400 of FIG. 4 are annotated with identifier numbers to indicate utilization of the tools of FIG. 3 with a corresponding identifier number, as indicated in column 310, to perform such steps.

Workflow 400 starts at step 402, where it is determined whether one or more tumors are detected in the one or more medical images. The detection of the one or more tumors from the one or more input medical images is determined using tumor detector tool 302-A of FIG. 3, as indicated by the annotation of step 402 with identifier number 1.

In response to determining that no tumors are detected in the one or more medical images at step 402, a T-stage of Tx is assigned at step 404. User input may be received manually defining the T-stage based on the one or more tumors in the one or more medical images. The user input may be received from a user (e.g., a clinician or a radiologist) via manual input tool 306-A of FIG. 3, as indicated by the annotation of step 404 with identifier number 9. Workflow 400 then proceeds to step 406 for N-staging the one or more tumors, as further described below with respect to step 108 of FIG. 1.

In response to determining that at least one tumor is detected in the one or more medical images at step 402, the number of the at least one tumor detected in the one or more medical images that are likely to be malignant is determined at step 408. The number of the at least one tumor likely to be malignant is determined using tumor classifier tool 302-B of FIG. 3, as indicated by the annotation of step 408 with identifier number 2.

In response to determining that none of the at least one tumor is likely to be malignant at step 408, workflow 400 proceeds to step 404 and stage Tx is assigned.

In response to determining that only one of the at least one tumor is likely to be malignant at step 408, it is determined whether a location of the malignant tumor conforms with the one or more biopsy reports at step 410. In response to determining that the location of the malignant tumor conforms with the one or more biopsy reports at step 410, T-staging is performed at step 412. The T-staging is performed using tumor size tool 302-C, primary tumor locater tool 302-E, tumor location by anatomy tool 302-F, and text input tool 306-B, as indicated by the annotations of step 412 with identifier numbers 3, 5, 6, and 10 respectively. The T-staging is further described below with respect to step 106 of FIG. 1. In response to determining that the location of the malignant tumor does not conform with the one or more biopsy reports at step 410, an indication that the malignant tumor cannot be staged is returned at step 414. User input may be received manually defining the T-stage via manual input tool 306-A of FIG. 3, as indicated by the annotation of step 404 with identifier number 9.

In response to determining that more than one of the at least one tumor is likely to be malignant at step 408, it is determined whether the locations of each of the malignant tumors conform with the one or more biopsy reports at step 416. The determination of whether the locations of each of the malignant tumors conforms with the one or more biopsy reports is performed using tumor size tool 302-C, primary tumor locater tool 302-E, tumor location by anatomy tool 302-F, and text input tool 306-B, as indicated by the annotations of step 412 with identifier numbers 3, 5, 6, and 10 respectively.

In response to determining that the locations of each of the malignant tumors conform with the one or more biopsy reports at step 416, each of the malignant tumors are separately T-staged at step 418. User input may be received selecting each of the malignant tumors for the T-staging via manual input tool 306-A of FIG. 3, as indicated by the annotation of step 418 with identifier number 9. Workflow 400 proceeds to step 412 for the T-staging.

In response to determining that the locations of each of the malignant tumors do not conform with the one or more biopsy reports at step 416, malignant tumors that conform with the one or more biopsy reports are selected at step 420. User input may be received selecting the conforming malignant tumors for the T-staging via manual input tool 306-A of FIG. 3, as indicated by the annotation of step 420 with identifier number 9. Each of the selected conforming malignant tumors are T-staged separately at step 422 and workflow 400 proceeds to step 412 for T-staging. If none of the malignant tumors are selected as conforming with the one or more biopsy reports at step 420, stage Tx is assigned at step 424. User input may be received manually defining the T-stage of the one or more tumors in the one or more medical images. The user input may be received from a user (e.g., a clinician or a radiologist) via manual input tool 306-A of FIG. 3, as indicated by the annotation of step 424 with identifier number 9. Workflow 400 then proceeds to step 426 for N-staging the one or more tumors, as further described below with respect to step 108 of FIG. 1.

Workflow 400 confirms that each tumor (detected by tumor detector tool 302-A of FIG. 3) has a size (determined by tumor size tool 302-C), location in the lung (determined by primary tumor locater tool 302-E), and surrounding anatomy (determined by tumor location by anatomy tool 302-F) that matches the text of the one or more biopsy reports (input via text input tool 306-B). If the detected tumor is considered malignant (determined by tumor classifier tool 302-B) but does not match the one or more biopsy reports, a decision as to how to proceed is entered manually (using manual input tool 306-A).

At step 106 of FIG. 1, in response to determining that the detection and the malignancy classification conform to the one or more biopsy reports (at step 104 of FIG. 1), a T-stage of the cancer is determined based on a location and a size of the one or more tumors determined based on the patient data. The T-stage represents the size of the primary tumor and the extent that the primary tumor has invaded nearby tissue. A primary tumor (also referred to as an original tumor) refers to a tumor that is at the original anatomical site where it first arose. In one embodiment, the T-stage of the one or more tumors is determined as one of Tx, T1, T2, T3, and T4, where T1 may be substaged into T1a, T1b, and T1c and T2 may be substaged into T2a and T2b.

In one example, as shown in FIG. 2, a T-stage is determined at stage 204 of workflow 200. In stage 204, a T-stage is determined at step 216 by a T-stager based on size and location of the primary tumors. The T-stage may be determined by performing a T1 substaging at step 218 to determine the T-stage as being Stage T1a, T1b, or T1 c at step 220, a T2 substaging at step 222 to determine the T-stage as being T2a or T2b at step 224, or may determine the T-stage of the one or more tumors as being Stage T3 at step 226 or Stage T4 at step 228. Stage 204 of workflow 200 is described in further detail below with respect to FIG. 5.

Figure 5:
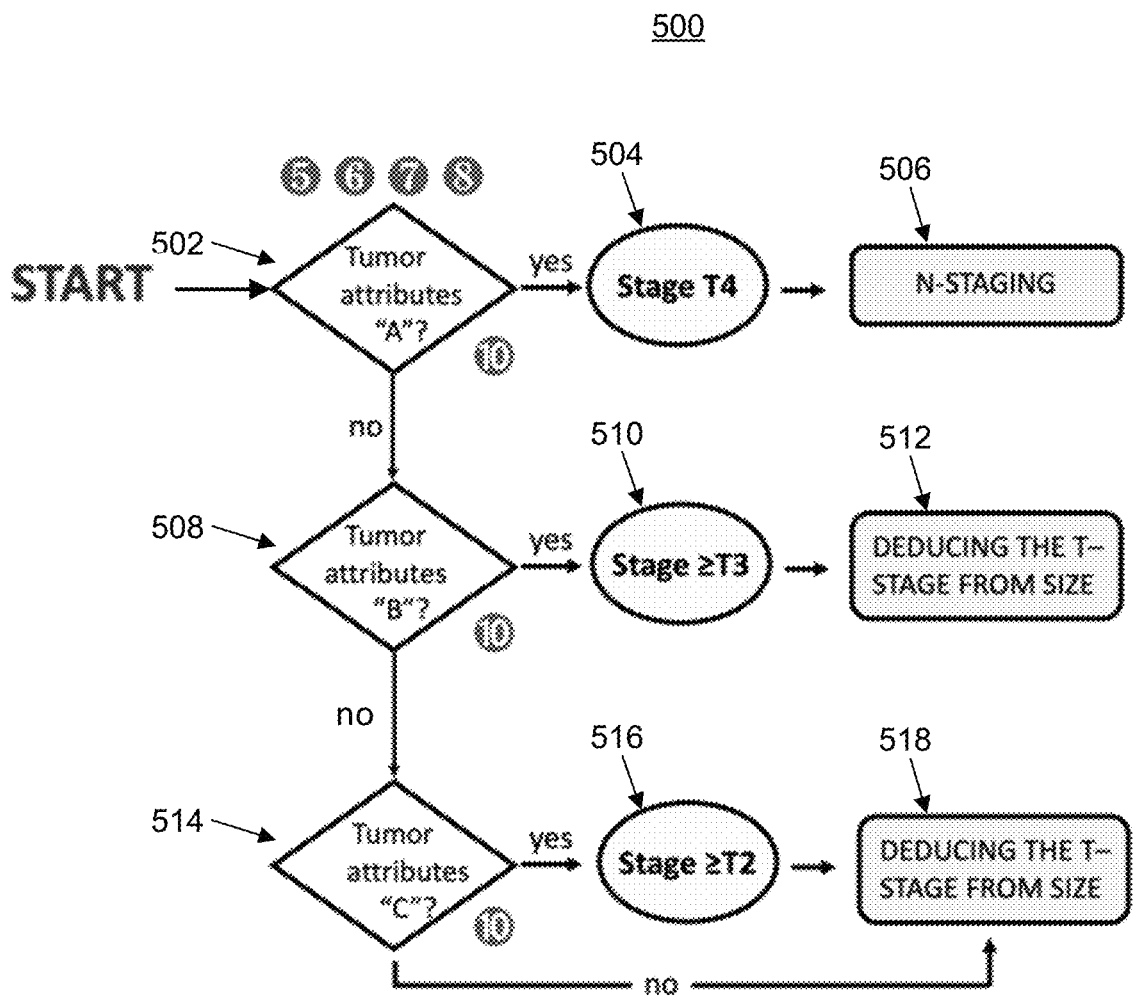
FIG. 5 shows a workflow for determining a T-stage of a cancer, in accordance with one or more embodiments.

FIG. 5 shows a workflow 500 for determining a T-stage of a cancer, in accordance with one or more embodiments. Workflow 500 may be performed at step 106 of FIG. 1 or at step 216 of workflow 200. Certain steps of workflow 500 of FIG. 5 are annotated with identifier numbers to indicate utilization of the tools of FIG. 3 with a corresponding identifier number, as indicated in column 310, to perform such steps. Workflow 500 determines the T-stage of the cancer based on a location, size, and multiplicity of a primary tumor.

At step 502 of FIG. 5, it is determined whether the tumor has tumor attributes "A". As used herein, a tumor has tumor attributes "A" if the tumor 1) invades one or more of the diaphragm, mediastinum, heart, great vessels, trachea, recurrent laryngeal nerve, esophagus, or vertebral body or carina, or 2) is a separate tumor nodule in an ipsilateral lobe different from that of the primary. The tumor may be of any size. The determination of whether the tumor has tumor attributes "A" is performed based on the tumor location using primary tumor locater tool 302-E, tumor location by anatomy tool 302-F, anatomy identifier tool 304-A, and pneumonitis/effusions/atelectasis classifier tool 304-B, as indicated by the annotations of step 502 with identifier numbers 5, 6, 7, and 8 respectively. User input may be received assigning the tumor with a descriptor A via text input tool 306-B, as indicated by the annotation of step 502 with identifier number 10. In response to determining that the tumor has tumor attributes "A" at step 502, the tumor is determined to have a T-stage of T4 at step 504. Workflow 500 then proceeds to step 506 for N-staging the tumor, as further described below with respect to step 108 of FIG. 1.

In response to determining that the tumor does not have tumor attributes "A" at step 502, it is determined whether the tumor has tumor attributes "B" at step 508. As used herein, the tumor has tumor attributes "B" if the tumor 1) directly invades one or more of the parietal pleural (PL3), chest wall (including the superior sulcus tumors), phrenic nerve, or parietal pericardium, or 2) is a separate tumor nodule in the same lobe as the primary. The determination of whether the tumor has tumor attributes "B" is performed based on the tumor location using primary tumor locater tool 302-E, tumor location by anatomy tool 302-F, anatomy identifier tool 304-A, and pneumonitis/effusions/atelectasis classifier tool 304-B. User input may be received assigning the tumor a descriptor B via text input tool 306-B, as indicated by the annotation of step 508 with identifier number 10. In response to determining that the tumor has tumor attributes "B" at step 508, the tumor is determined to have a T-stage of T3 or higher at step 510. Workflow 500 then proceeds to step 512 for further determining the T-stage based on a size of the tumor, described in more detail below with respect to FIG. 6.

In response to determining that the tumor does not have tumor attributes "B" at step 508, it is determined whether the tumor has tumor attributes "C" at step 514. As used herein, the tumor has tumor attributes "C" if the tumor 1) involves the main bronchus regardless of distance to the carina but without involvement of the carina, or 2) invades the visceral pleura (PL1 or PL2), or 3) is associated with the atelectasis or obstructive pneumonitis extending to the hilar region, involving part or all of the lung. The determination of whether the tumor has tumor attributes "C" is performed based on the tumor location using primary tumor locater tool 302-E, tumor location by anatomy tool 302-F, anatomy identifier tool 304-A, and pneumonitis/effusions/atelectasis classifier tool 304-B. User input may be received assigning the tumor a descriptor C via text input tool 306-B, as indicated by the annotation of step 514 with identifier number 10. In response to determining that the tumor has tumor attributes "C" at step 514, the tumor is determined to have a T-stage of T2 or higher at step 516. Workflow 500 then proceeds to step 518 for further determining the T-stage based on a size of the tumor, described in more detail below with respect to FIG. 6. In response to determining that the tumor does not have tumor attributes "C" at step 514, workflow 500 proceeds directly to step 518 for further determining the T-stage based on a size of the tumor.

Figure 6:
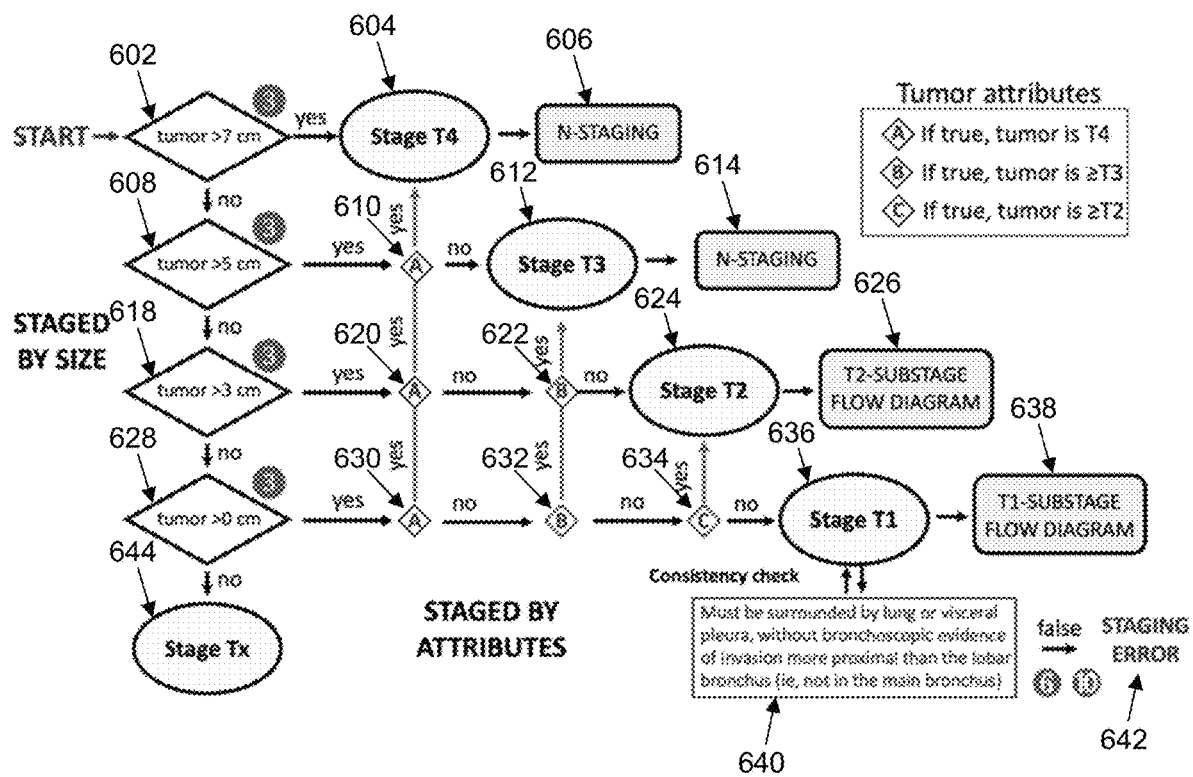
FIG. 6 shows a workflow for further determining a T-stage of a cancer based on tumor size and attributes, in accordance with one or more embodiments.

FIG. 6 shows a workflow 600 for further determining a T-stage of a cancer based on tumor size and attributes, in accordance with one or more embodiments. Workflow 600 may be performed at steps 512 and 518 of workflow 500 of FIG. 5. Certain steps of workflow 600 of FIG. 6 are annotated with identifier numbers to indicate utilization of the tools of FIG. 3 with a corresponding identifier number, as indicated in column 310, to perform such steps. Workflow 600 may be represented as a grid with the tumor location attribute on the horizontal axis and the tumor size as the vertical axis.

Workflow 600 starts at step 602, where it is determined whether a tumor has a size greater than 7 cm (centimeters). The determination of the tumor size is performed using tumor size tool 302-C, as indicated by the annotation of step 602 with identifier number 3. In response to determining that the tumor has a size greater than 7 cm at step 602, the cancer is determined to have a T-stage of T4 at step 604. Workflow 600 then proceeds to step 606 for N-staging, as further described below with respect to step 108 of FIG. 1.

In response to determining that the tumor does not have a size greater than 7 cm at step 602, it is determined whether the tumor has a size greater than 5 cm at step 608. The determination of the tumor size is performed using tumor size tool 302-C, as indicated by the annotation of step 608 with identifier number 3. In response to determining that the tumor has a size greater than 5 cm at step 608, it is determined whether the tumor has tumor attributes "A" at step 610. In response to determining that the tumor has tumor attributes "A" at step 610, the cancer is determined to have a T-stage of T4 at step 604. In response to determining that the tumor does not have tumor attributes "A" at step 610, the cancer is determined to have a T-stage of T3 at step 612. Workflow 600 then proceeds to step 614 for N-staging, as further described below with respect to step 108 of FIG. 1.

In response to determining that the tumor does not have a size greater than 5 cm at step 608, it is determined whether the tumor has a size greater than 3 cm at step 618. The determination of the tumor size is performed using tumor size tool 302-C, as indicated by the annotation of step 618 with identifier number 3. In response to determining that the tumor has a size greater than 3 cm at step 618, it is determined whether the tumor has tumor attributes "A" at step 620. In response to determining that the tumor has tumor attributes "A" at step 620, the cancer is determined to have a T-stage of T4 at step 604. In response to determining that the tumor does not have tumor attributes "A" at step 620, it is determined whether the tumor has tumor attributes "B" at step 622. In response to determining that the tumor has tumor attributes "B" at step 622, the cancer is determined to have a T-stage of T3 at step 612. In response to determining that the tumor does not have tumor attributes "B" at step 622, the cancer is determined to have a T-stage of T2 at step 624. Workflow 600 proceeds to step 626 for T2-substaging, as further described below with respect to FIG. 8.

In response to determining that the tumor does not have a size greater than 3 cm at step 618, it is determined whether the tumor has a size greater than 0 cm at step 628. The determination of the tumor size is performed using tumor size tool 302-C, as indicated by the annotation of step 628 with identifier number 3. In response to determining that the tumor has a size greater than 0 cm at step 628, it is determined whether the tumor has tumor attributes "A" at step 630. In response to determining that the tumor has tumor attributes "A" at step 630, the cancer is determined to have a T-stage of T4 at step 604. In response to determining that the tumor does not have tumor attributes "A" at step 630, it is determined whether the tumor has tumor attributes "B" at step 632. In response to determining that the tumor has tumor attributes "B" at step 632, the cancer is determined to have a T-stage of T3 at step 612. In response to determining that the tumor does not have tumor attributes "B" at step 632, it is determined whether the tumor has tumor attributes "C" at step 634. In response to determining that the tumor has tumor attributes "C" at step 634, the cancer is determined to have a T-stage of T2 at step 624. In response to determining that the tumor does not have tumor attributes "C" at step 634, the cancer is determined to have a T-stage of T1 at step 636. Workflow 600 proceeds to step 638 for T1-substaging, as further described below with respect to FIG. 7.

A T1 consistency check is performed at step 640. The T1 consistency check is performed using tumor location by anatomy tool 302-F and text input tool 306-B, as indicated by the annotation of step 640 with identifier numbers 6 and 10 respectively. In the T1 consistency check, it is determined whether the tumor is surrounded by lung or visceral pleura, without bronchoscopic evidence of invasion more proximal than the lobar bronchus (i.e., not in the main bronchus). If so, the T-stage of T1 at step 636 is consistent. If not, a staging error is returned at step 642.

In response to determining that the tumor does not have a size greater than 0 cm at step 628, a T-stage of Tx is assigned at step 644.

Figure 7:
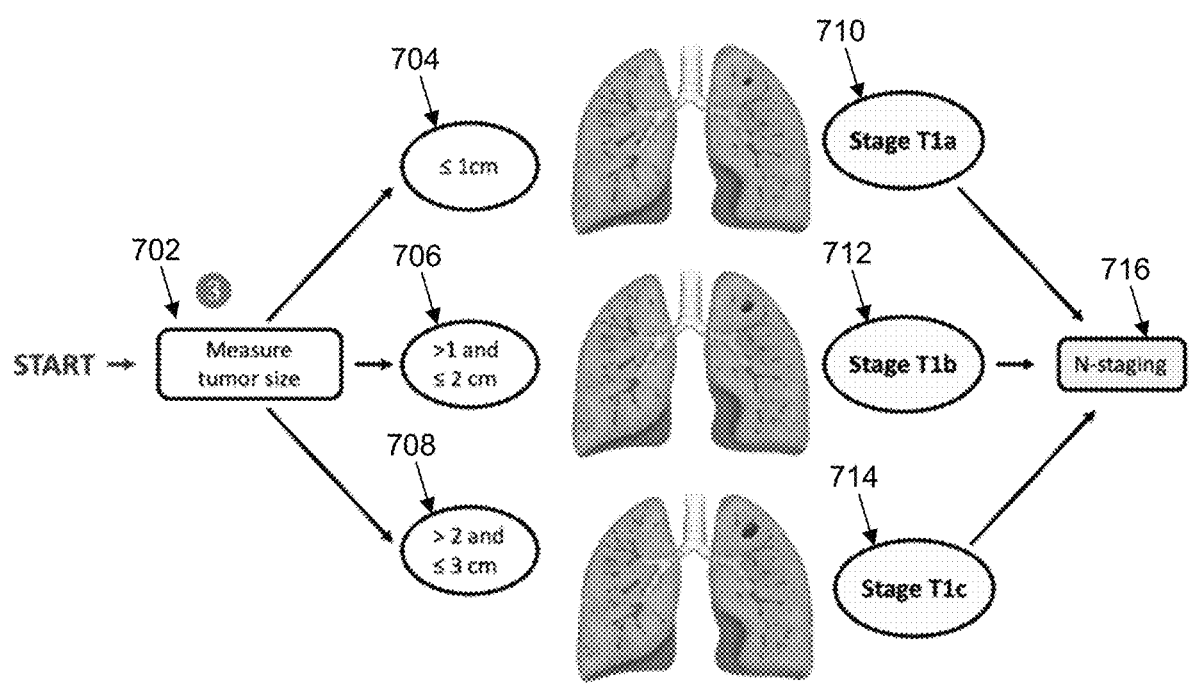
FIG. 7 shows a workflow for T1-substaging a tumor, in accordance with one or more embodiments.

FIG. 7 shows a workflow 700 for T1-substaging a tumor, in accordance with one or more embodiments. Workflow 700 may be performed at step 218 of FIG. 2 or step 638 of FIG. 6. Certain steps of workflow 700 of FIG. 7 are annotated with identifier numbers to indicate utilization of the tools of FIG. 3 with a corresponding identifier number, as indicated in column 310, to perform such steps.

Workflow 700 starts at step 702, where the tumor size of the tumor is determined. The determination of the tumor size is performed using tumor size tool 302-C, as indicated by the annotation of step 702 with identifier number 3. In response to determining that the tumor size of the tumor is less than or equal to 1 cm at step 704, the cancer is determined to have a T-stage of stage T1a at step 710 and workflow 700 proceeds to step 716 for N-staging. In response to determining that the tumor size of the tumor is greater than 1 cm and less than or equal to 2 cm at step 706, the cancer is determined to have a T-stage of stage T1b at step 712 and workflow 700 proceeds to step 716 for N-staging. In response to determining that the tumor size of the tumor is greater than 2 cm and less than or equal to 3 cm at step 708, the cancer is determined to have a T-stage of stage T1c at step 714 and workflow 700 proceeds to step 716 for N-staging. N-staging at step 716 is further described below with respect to step 108 of FIG. 1.

Figure 8:
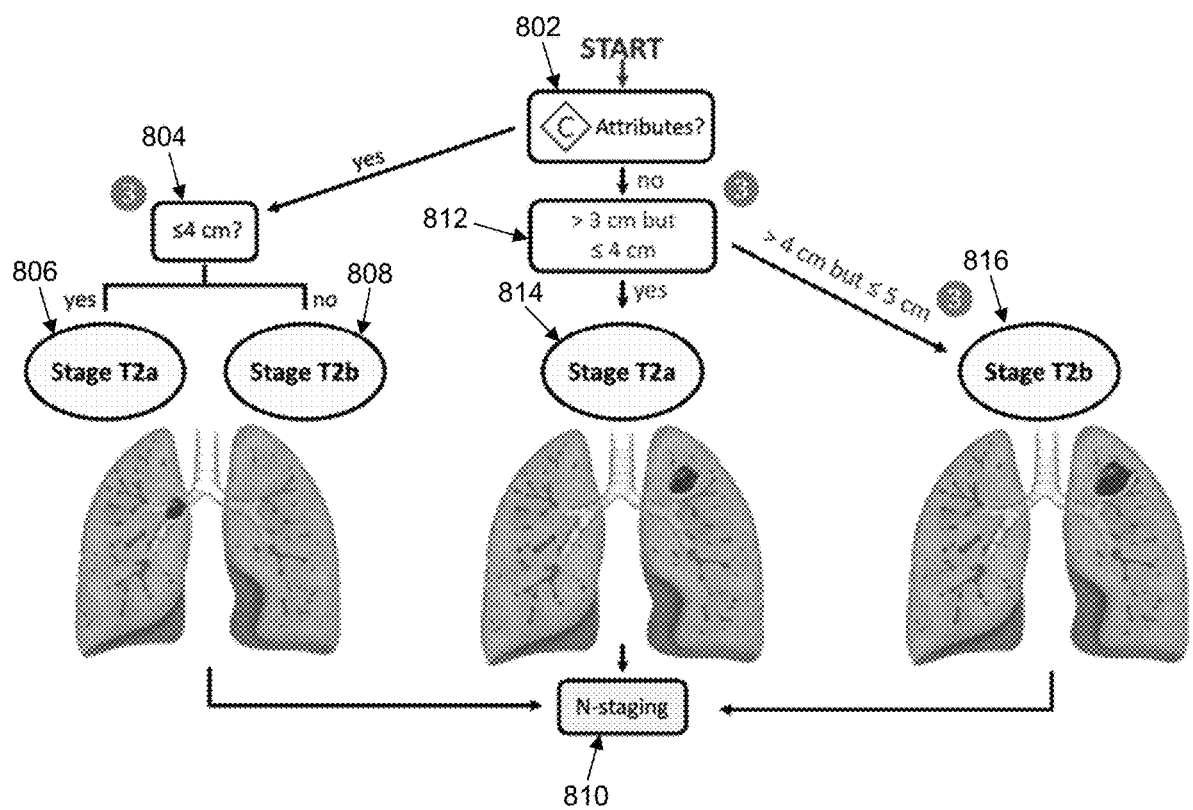
FIG. 8 shows a workflow for T2-substaging of a tumor, in accordance with one or more embodiments.

FIG. 8 shows a workflow 800 for T2-substaging of a tumor, in accordance with one or more embodiments. Workflow 800 may be performed at step 222 of FIG. 2 or step 626 of FIG. 6. Certain steps of workflow 800 of FIG. 8 are annotated with identifier numbers to indicate utilization of the tools of FIG. 3 with a corresponding identifier number, as indicated in column 310, to perform such steps.

Workflow 800 starts at step 802, where it is determined whether the tumor has tumor attributes "C". In response to determining that the tumor has tumor attributes "C" at step 802, it is determined whether the tumor size of the tumor is less than or equal to 4 cm at step 804. The determination of the tumor size is performed using tumor size tool 302-C, as indicated by the annotation of step 804 with identifier number 3. In response to determining that the tumor size of the tumor is less than or equal to 4 cm at step 804, the cancer is determined to have a T-stage of Stage T2a at step 806. In response to determining that the tumor size of the tumor is not less than or equal to 4 cm (i.e., is greater than 4 cm) at step 804, the cancer is determined to have a T-stage of Stage T2b at step 808.

In response to determining that the tumor does not have tumor attributes "C" at step 802, it is determined whether the tumor size of the tumor is greater than 3 cm but less than or equal to 4 cm at step 812. The determination of the tumor size is performed using tumor size tool 302-C, as indicated by the annotation of step 812 with identifier number 3. In response to determining that the tumor size of the tumor is greater than 3 cm but less than or equal to 4 cm at step 812, the cancer is determined to have a T-stage of Stage T2a at step 814. In response to determining that the tumor size of the tumor is greater than 4 cm but less than or equal to 5 cm, the cancer is determined to have a T-stage of Stage T2b at step 816. Workflow 800 proceeds from steps 806, 808, 814, or 816 to step 810 for N-staging, which is further described below with respect to step 108 of FIG. 1.

Returning to step 106 of FIG. 1, a tumor of any size that invades the RLN (recurrent laryngeal nerve) is, by definition, determined to have a T-stage of T4. However, direct automatic segmentation of the RLN may not be robust and therefore may not be able to reliably locate the tumor. In accordance with embodiments described herein, a tumor T, N, or M classification tool 302-D is provided for differentiating between primary tumors and enlarged nodes in the mediastinum for localizing the tumor. A clinical indicator of involvement of the left RLN with a tumor is the onset of chronic hoarseness due to paralysis of the left vocal fold (cord). This can happen due to the primary tumor extending into the AP (aorto-pulmonary) space where the left RLN loops around the aorta (resulting in the tumor having a T-stage of T4) or due to unseen mediastinal lymph nodes (resulting in the tumor having an N-stage of N2). The tumor T, N, or M classification tool 302-D receives user input of clinical data relating to the onset of a paralyzed nerve via manual input tool 306-A for classifying the tumor as being primary, hilar, mediastinal, or metastatic.

Involvement of the phrenic nerve is also one of the criteria for determining a T-stage of the tumor. If the primary tumor encases the phrenic nerve, the T-stage of the tumor is stage T3 or greater. As in the case of the RLN, a segmentation of the phrenic nerve may not be robust. In one embodiment, the primary tumor is determined to involve the area around the phrenic nerve, even if not depicted in the one or more medical images, where the diaphragm (on the same side as the tumor) is at least partially paralyzed. Paralysis of the at least one diaphragm may be received as user input via manual input tool 306-A.

At step 108 of FIG. 1, an N-stage of the cancer is determined by combining a metastasis evaluation of the cancer to regional lymph nodes determined from the one or more medical images and metastasis evaluation of the cancer in the regional lymph nodes determined from the one or more biopsy reports. The N-stage represents the extent that the one or more tumors have invaded nearby (regional)

lymph nodes. In one embodiment, the N-stage of the one or more tumors is determined as one of N0, N1, N2, and N3. N0 indicates there is no cancer in regional lymph nodes. N1, N2, and N3 refer to the number and location of regional lymph nodes that include cancer, where the higher the N number the more regional lymph nodes that include the cancer.

In one example, as shown in FIG. 2, an N-stage of the one or more tumors is determined at stage 206 of workflow 200. In stage 206, an N-stage of the one or more tumors is determined at step 230 by an N-stager to determine the N-stage of the one or more tumors as being Stage N0 at step 232, Stage N1 at step 234, Stage N2 at step 236, or Stage N3 at step 238.

N-staging of the cancer differs from T-staging in that, in addition to the one or more medical images, the N-stage may also be determined using EBUS (endobronchial ultrasound) in one embodiment. Although EBUS may output medical images, such medical images are not suitable for automatic or human analysis and can only be interpreted by biopsy. Accordingly, in one embodiment, the N-stage of the cancer is determined based on a metastasis evaluation of the cancer determined from the one or more medical images and a metastasis evaluation of the cancer determined from the one or more biopsy reports.

In one embodiment, the metastasis evaluation of the cancer determined from the one or more medical images and the metastasis evaluation of the cancer determined from the one or more biopsy reports are combined to yield a single malignancy result. The combining is performed by comparing the metastasis evaluation of the cancer determined from the one or more medical images and the metastasis evaluation of the cancer determined from the one or more biopsy reports based on the following levels of evidence. Level one evidence, the highest level of evidence, is a positive biopsy result (indicating that the cancer has metastasized to that region) in the one or more biopsy reports. The region of the biopsy in the one or more medical images will be labelled "positive". Level two evidence is negative metastasis regions (indicating that the cancer has not metastasized to that region) determined from the one or more medical images (e.g., a PET negative region). The negative regions can be overridden only by a positive biopsy in the one or more biopsy reports. That is because such negative regions are usually accurate unless the tumor is very small (e.g., less than 1 cm) or is of low biologic activity (e.g., in-situ or minimally invasive adenocarcinoma). Level three evidence is a negative biopsy result (indicating that the cancer has not metastasized to that region) in the one or more biopsy reports. The negative biopsy is only considered level three evidence because the negative biopsy may be due to the tumor being missed. Level four evidence, the lowest level of evidence, is positive metastasis regions (indicating that the cancer has metastasized to that region) determined from the one or more medical images (e.g., a PET positive region).

The positive and negative regions are determined from the one or more medical images by first segmenting regional lymph node stations from the medical images using lymph node annotator tool 308-A. The biopsy results are determined from the one or more biopsy reports using text input tool 306-A. Text-to-image tool 306-C converts the biopsy results to a positive or negative label of the corresponding lymph node stations in the medical images.

Figure 9:
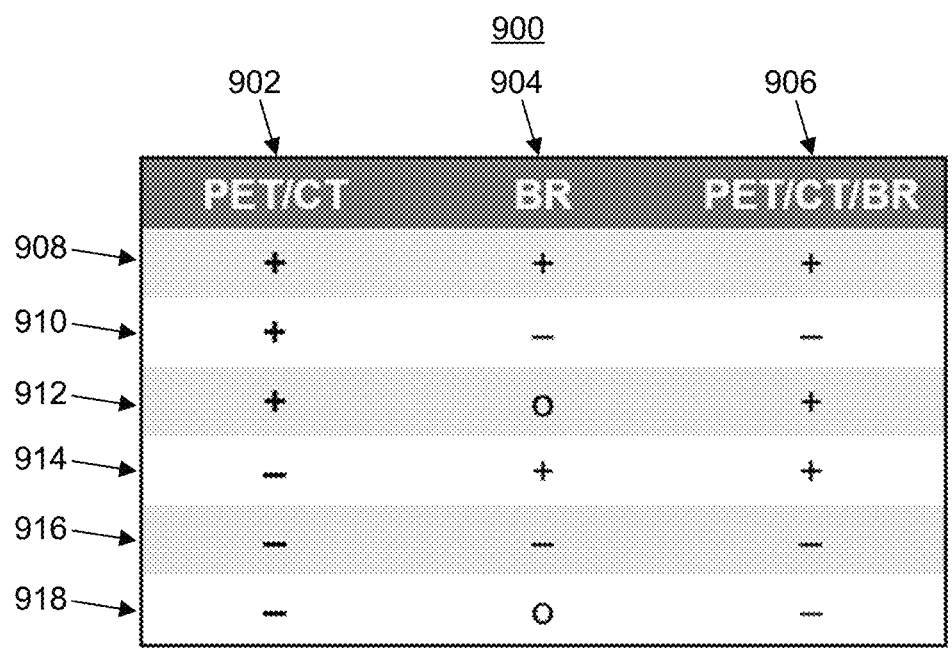
FIG. 9 shows a table for combining a metastasis evaluation of the cancer determined from PET/CT medical images and a metastasis evaluation of the cancer determined from a biopsy report, in accordance with one or more embodiments.

FIG. 9 shows a table 900 for combining a metastasis evaluation of the cancer determined from PET/CT medical images and a metastasis evaluation of the cancer determined from a biopsy report (BR), in accordance with one or more embodiments. Column 902 represents PET/CT results indicating a metastasis evaluation of the cancer determined from PET/CT medical images. Column 904 represents biopsy report results indicating a metastasis evaluation of the cancer determined from a biopsy report. Column 906 represents a combined metastasis result (PET/CT/BR) determined by comparing columns 902 and 904 according to the levels of evidence. In table 900, + indicates positive (i.e., metastasized), − indicates negative (i.e., not metastasized), and o indicates incomplete. As can be seen in rows 908 and 916, where the PET/CT results in column 902 and the BR results in column 904 are the same (both positive or both negative), the combined metastasis result in column 906 will also be the same (positive or negative respectively). Where PET/CT results in column 902 is positive and BR results in column 904 is negative as shown in row 910, the combined metastasis result in column 906 is negative since the negative BR results is level three evidence while the PET/CT results is level four evidence. Where PET/CT results in column 902 is negative and BR results in column 904 is positive as shown in row 914, the combined metastasis result in column 906 is positive since the positive BR results is level one evidence while the PET/CT results is level two evidence. Where the BR results in column 904 is incomplete, the combined metastasis result in column 906 will be the same as the PET/CT result in column 902, as shown in rows 912 and 918.

Figure 10:
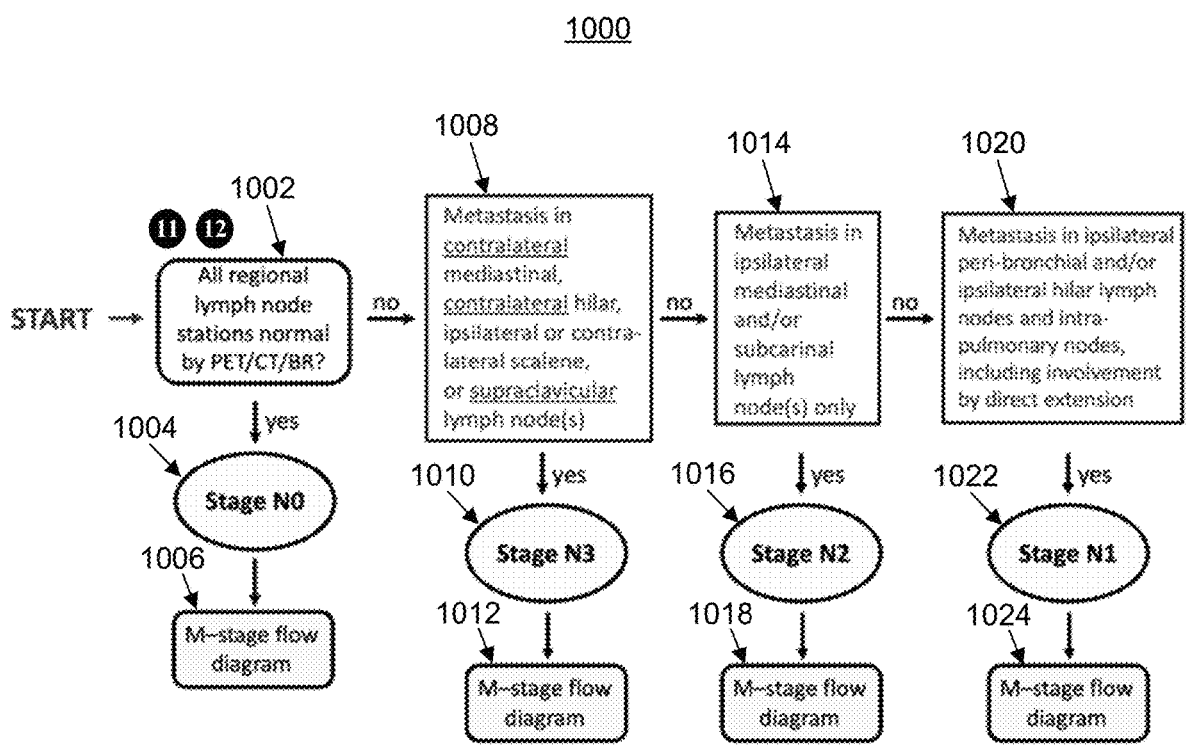
FIG. 10 shows a workflow for determining an N-stage of a tumor based on combined PET/CT/BR metastasis results, in accordance with one or more embodiments.

FIG. 10 shows a workflow 1000 for determining an N-stage of a tumor based on combined PET/CT/BR metastasis results, in accordance with one or more embodiments. Workflow 1000 may be performed at step 108 of FIG. 1 or at step 230 of FIG. 2. Certain steps of workflow 1000 of FIG. 10 may be performed using one or more tools of FIG. 3.

Workflow 1000 starts at step 1002, where it is determined whether all regional lymph node stations are normal (i.e., no metastasis of the cancer) according on the combined PET/CT/BR metastasis results. The determination of whether all regional lymph node stations are normal at step 1002 is performed using test-to-image tool 306-C and lymph node annotator tool 308-A, as indicated by the annotation of step 1002 with identifier number 11 and 12 respectively. In response to determining that all regional lymph node stations are normal at step 1002, the tumor is determined to have an N-stage of N0 at step 1004. Workflow 1000 proceeds to step 1006 for M-staging the tumor, as described in further detail below with respect to step 110 of FIG. 1.

In response to determining that all regional lymph node stations are not normal at step 1002, it is determined whether there is metastasis of the cancer in the contralateral mediastinal, the contralateral hilar, the ipsilateral or contralateral scalene, or the supraclavicular lymph nodes at step 1008. In response to determining that there is metastasis at step 1008, the tumor is determined to have an N-stage of N3 at step 1010. Workflow 1000 proceeds to step 1012 for M-staging the tumor, as described in further detail below with respect to step 110 of FIG. 1.

In response to determining that there is no metastasis at step 1008, it is determined whether there is metastasis of the cancer in the ipsilateral mediastinal and/or subcarinal lymph nodes only at step 1014. In response to determining that there is metastasis at step 1014, the tumor is determined to have an N-stage of N2 at step 1016. Workflow 1000 proceeds to step 1018 for M-staging the tumor, as described in further detail below with respect to step 110 of FIG. 1.

In response to determining that there is no metastasis at step 1014, it is determined whether there is metastasis of the cancer in the ipsilateral peri-bronchial and/or ipsilateral hilar lymph nodes and intra-pulmonary nodes (including involvement by direct extension) at step 1020. In response to determining that there is metastasis at step 1020, the tumor is determined to have an N-stage of N1 at step 1022. Workflow 1000 proceeds to step 1024 for M-staging the tumor, as described in further detail below with respect to step 110 of FIG. 1.

At step 110 of FIG. 1, an M-stage of the one or more tumors is determined. The M-stage represents distant metastasis (spread of cancer from one region of the patient to another). In one embodiment, the M-stage of the one or more tumors is determined as one of M0, M1a, M1b, and M1c. M0 represents no spread to other regions of the patient. M1a represents that cancer has spread to either both lungs, the fluid in the pericardium around the heart, or any tissue around the lungs. M1b represents that cancer has spread to a single area in an organ beyond the chest cavity. M1c represents that cancer is present in multiple lymph nodes or organs beyond the chest cavity.

In one example, as shown in FIG. 2, the M-stage of the one or more tumors is determined at stage 208 of workflow 200. In stage 208, an M-stage of the one or more tumors is determined at step 240 by an M-stager. The M-stage is determined as one of Stage M1c at step 242, Stage M1b at step 244, Stage M1a at step 246, or Stage M0 at step 248 according to a hierarchical analysis. Stage 208 is described in further detail below with respect to FIG. 11.

Figure 11:
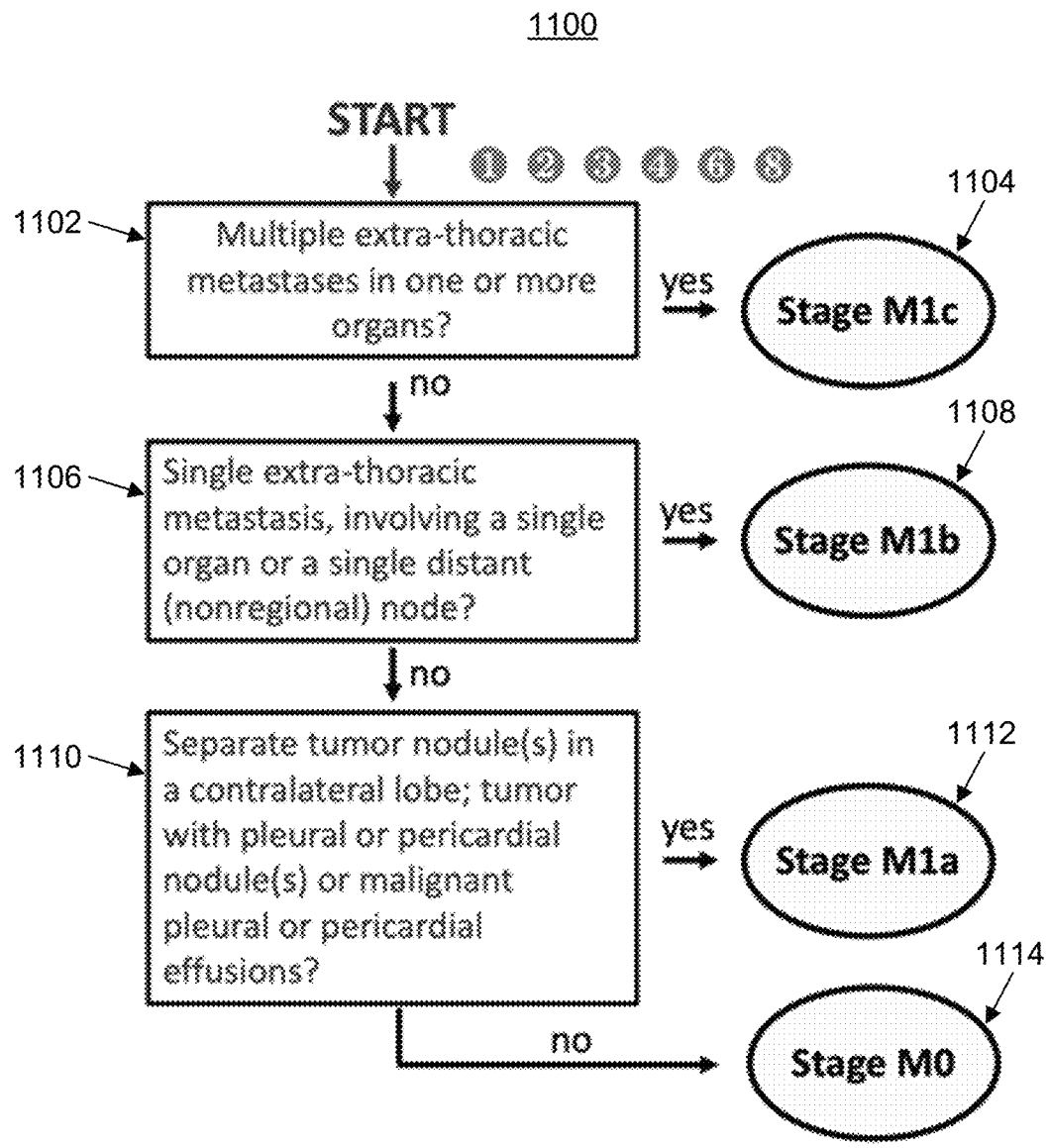
FIG. 11 shows a workflow for determining an M-stage of a tumor, in accordance with one or more embodiments.

FIG. 11 shows a workflow 1100 for determining an M-stage of a tumor, in accordance with one or more embodiments. Workflow 1100 may be performed at step 110 of FIG. 1 or at step 240 of workflow of FIG. 2. Steps 1102, 1106, and 1110 of workflow 1100 are performed utilizing tumor detector tool 302-A, tumor classifier tool 302-B, tumor size tool 302-C, tumor T, N, or M tool 302-D, tumor location by anatomy tool 302-F, and pneumonitis/effusions/atelectasis tool 304-B, respectively corresponding to identifier numbers 1, 2, 3, 4, 6, and 8.

At step 1102 of FIG. 11, it is determined whether there are multiple (two or more) extra-thoracic metastases of the cancer in one or more organs. In response to determining that there are multiple extra-thoracic metastases in one or more organs at step 1102, the M-stage is determined to be Stage M1c at step 1104.

In response to determining that there are not multiple extra-thoracic metastases in one or more organs at step 1102, it is determined whether there is a single extra-thoracic metastasis of the cancer, involving a single organ or a single distant (nonregional) node at step 1106. In response to determining that there is a single extra-thoracic metastasis involving a single organ or a single distant (nonregional) node at step 1106, the M-stage is determined to be Stage M1b at step 1108.

In response to determining that there is not a single extra-thoracic metastasis involving a single organ or a single distant (nonregional) node at step 1106, it is determined whether there is a separate tumor nodule in a contralateral lobe or whether there is a tumor with pleural or pericardial nodule or malignant pleural or pericardial effusions at step 1110. In response to determining that there is a separate tumor nodule in a contralateral lobe or that there is a tumor with pleural or pericardial nodule or malignant pleural or pericardial effusions at step 1110, the M-stage is determined to be Stage M1a at step 1112. In response to determining that there is not a separate tumor nodule in a contralateral lobe or that there is not a tumor with pleural or pericardial nodule or malignant pleural or pericardial effusions at step 1110, the M-stage is determined to be Stage M0 at step 1114.

At step 112 of FIG. 1, the T-stage, the N-stage, and the M-stage are output. For example, the T-stage, the N-stage, and the M-stage can be output by displaying the T-stage, the N-stage, and the M-stage on a display device of a computer system, storing the T-stage, the N-stage, and the M-stage on a memory or storage of a computer system, or by transmitting the T-stage, the N-stage, and the M-stage to a remote computer system.

Advantageously, embodiments described herein provide for an automatic staging system for staging cancer in patients. Such automatic staging system potentially save clinicians and other users a significant amount of time by automating almost all image-based and report-based analyses. The automated reporting reduces the work burden of radiologists, thus making the staging process much more efficient.

The automatic staging system provides for a hierarchical view to interpret staging decisions. The automatic staging system provides multiple modes in which a user can interact with it. For example, in one embodiment, once the system completes the auto-staging, a path along the series of decisions leading to the final TNM staging can be highlighted. In another embodiment, a user can trigger a switch from a default overview view to view a detailed view of each decision point by clicking on (or otherwise interacting with) the corresponding box (e.g., decision boxes in FIGS. 2, 4-8, and 10-11) and can return to the overview view via a "go back" button. At the detailed view of each decision point, the relevant anatomies, measurements, and findings detected by the system can be presented with dedicated visualization, as shown for example at FIG. 12.

Figure 12:
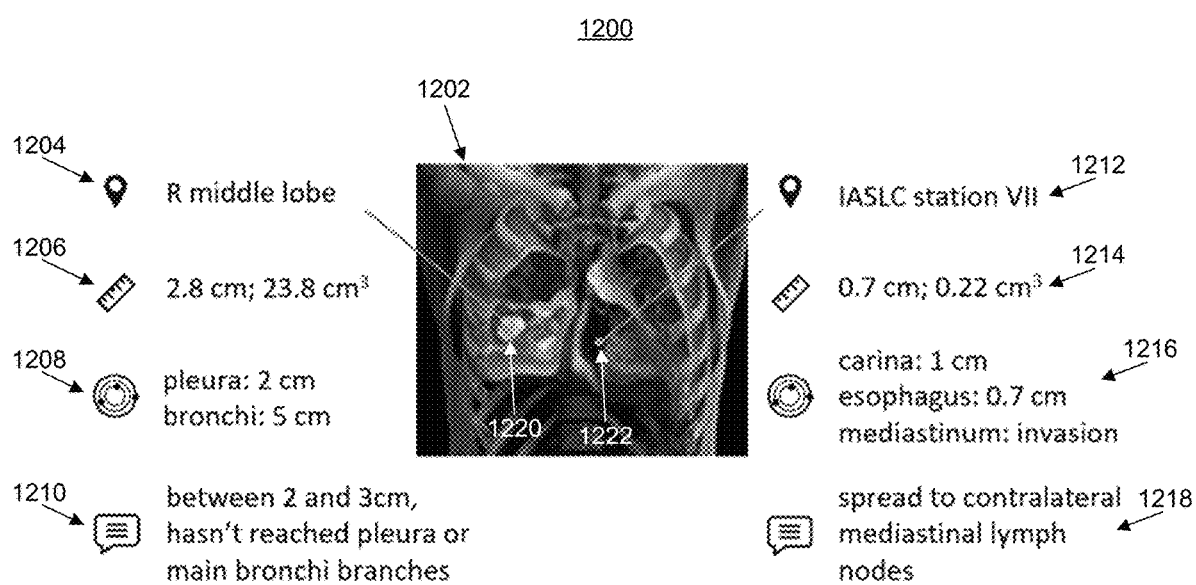
FIG. 12 shows a user interface visualizing anatomies, measurements, and findings, in accordance with one or more embodiments.

FIG. 12 shows a user interface 1200 visualizing anatomies, measurements, and findings, in accordance with one or more embodiments. User interface 1200 shows a medical image 1202 of tumors 1220 and 1222 on a lung annotated with findings determined in accordance with embodiments described herein. For example, medical image 1202 is respectively annotated with anatomy locations 1204 and 1212 of tumors 1220 and 1222, measurements 1206 and 1214 (e.g., diameter and volume) of tumors 1220 and 1222, measurements 1208 and 1216 of anatomies near tumors 1220 and 1222, and notes 1210 and 1218 relating to tumor 1220 and 1222.

In one embodiment, a user may edit or correct findings of the system at each decision point after reviewing and referencing the findings of the system with the TNM staging criteria. The correction made at any decision point is propagated automatically throughout the workflow, and the updated staging outcome may be displayed along with the updated path of decision points leading to the final TNM staging.

In one embodiment, a user may document supporting evidence (e.g., anatomies, measurements, and findings determined by the system), export the supporting evidence into tables/spreadsheets, and derive further clinically relevant descriptors. In one embodiment, the newly derived descriptors can be formulated as a function of the supporting evidence. A user can then exploratorily replace specific predefined criteria across the staging workflow with the relevant newly derived descriptors, which makes it more efficient for validating and discussing the user customized TNM staging. In one embodiment, a user may use the newly derived descriptors for analysis beyond TNM staging.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 13:
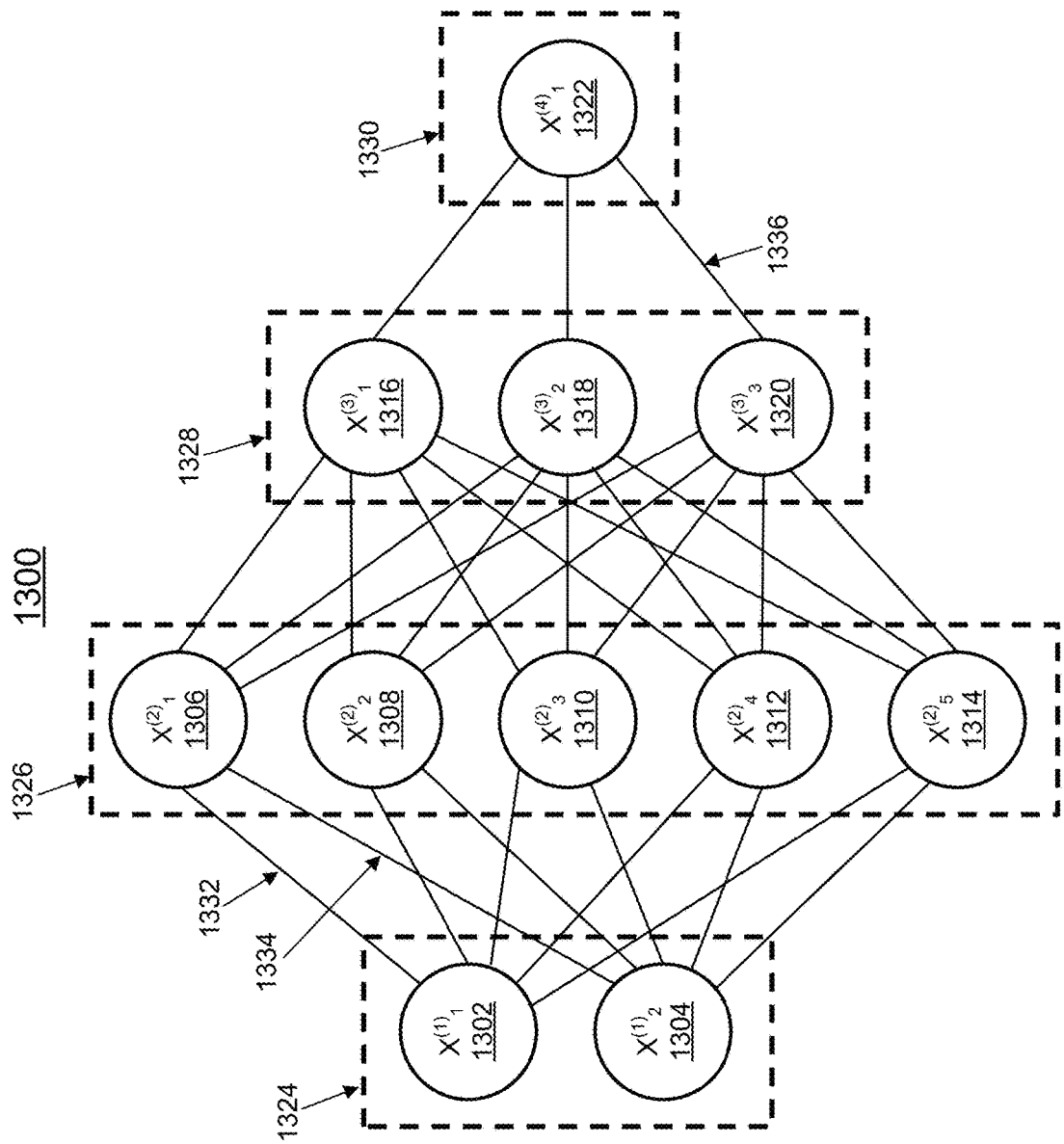
FIG. 13 shows an exemplary artificial neural network that may be used to implement one or more embodiments.

FIG. 13 shows an embodiment of an artificial neural network 1300, in accordance with one or more embodiments. Alternative terms for "artificial neural network" are "neural network", "artificial neural net" or "neural net". Machine learning networks described herein, such as, e.g., the machine learning based networks utilized for implementing tumor-centered tools 302, anatomy-centered tools 304, text manipulation tools 306, and lymph node station identifier tools 308 of FIG. 3, may be implemented using artificial neural network 1300.

The artificial neural network 1300 comprises nodes 1302-1322 and edges 1332, 1334, . . . , 1336, wherein each edge 1332, 1334, . . . , 1336 is a directed connection from a first node 1302-1322 to a second node 1302-1322. In general, the first node 1302-1322 and the second node 1302-1322 are different nodes 1302-1322, it is also possible that the first node 1302-1322 and the second node 1302-1322 are identical. For example, in FIG. 13, the edge 1332 is a directed connection from the node 1302 to the node 1306, and the edge 1334 is a directed connection from the node 1304 to the node 1306. An edge 1332, 1334, . . . , 1336 from a first node 1302-1322 to a second node 1302-1322 is also denoted as "ingoing edge" for the second node 1302-1322 and as "outgoing edge" for the first node 1302-1322.

In this embodiment, the nodes 1302-1322 of the artificial neural network 1300 can be arranged in layers 1324-1330, wherein the layers can comprise an intrinsic order introduced by the edges 1332, 1334, . . . , 1336 between the nodes 1302-1322. In particular, edges 1332, 1334, . . . , 1336 can exist only between neighboring layers of nodes. In the embodiment shown in FIG. 13, there is an input layer 1324 comprising only nodes 1302 and 1304 without an incoming edge, an output layer 1330 comprising only node 1322 without outgoing edges, and hidden layers 1326, 1328 in-between the input layer 1324 and the output layer 1330. In general, the number of hidden layers 1326, 1328 can be chosen arbitrarily. The number of nodes 1302 and 1304 within the input layer 1324 usually relates to the number of input values of the neural network 1300, and the number of nodes 1322 within the output layer 1330 usually relates to the number of output values of the neural network 1300.

In particular, a (real) number can be assigned as a value to every node 1302-1322 of the neural network 1300. Here, $x^{(n)}_i$ denotes the value of the i-th node 1302-1322 of the n-th layer 1324-1330. The values of the nodes 1302-1322 of the input layer 1324 are equivalent to the input values of the neural network 1300, the value of the node 1322 of the output layer 1330 is equivalent to the output value of the neural network 1300. Furthermore, each edge 1332, 1334, . . . , 1336 can comprise a weight being a real number, in particular, the weight is a real number within the interval $[-1, 1]$ or within the interval $[0, 1]$. Here, $w^{(m,n)}_{i,j}$ denotes the weight of the edge between the i-th node 1302-1322 of the m-th layer 1324-1330 and the j-th node 1302-1322 of the n-th layer 1324-1330. Furthermore, the abbreviation $w^{(n)}_{i,j}$ is defined for the weight $w^{(n,n+1)}_{i,j}$.

In particular, to calculate the output values of the neural network 1300, the input values are propagated through the neural network. In particular, the values of the nodes 1302-1322 of the (n+1)-th layer 1324-1330 can be calculated based on the values of the nodes 1302-1322 of the n-th layer 1324-1330 by $$x_j^{(n+1)} = f(\Sigma_i x_i^{(n)} \cdot w_{i,j}^{(n)}).$$

Herein, the function $f$ is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 1324 are given by the input of the neural network 1300, wherein values of the first hidden layer 1326 can be calculated based on the values of the input layer 1324 of the neural network, wherein values of the second hidden layer 1328 can be calculated based in the values of the first hidden layer 1326, etc.

In order to set the values $w^{(m,n)}_{i,j}$ for the edges, the neural network 1300 has to be trained using training data. In particular, training data comprises training input data and training output data (denoted as $t_i$). For a training step, the neural network 1300 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 1300 (backpropagation algorithm). In particular, the weights are changed according to $$w'_{i,j}{}^{(n)} = w_{i,j}{}^{(n)} - \gamma \cdot \delta_j{}^{(n)} \cdot x_i{}^{(n)}$$

wherein γ is a learning rate, and the numbers $\delta^{(n)}{}_j$ can be recursively calculated as $$\delta_j{}^{(n)} = (\Sigma_k \delta_k{}^{(n+1)} \cdot w_{j,k}{}^{(n+1)}) \cdot f'(\Sigma_i x_i{}^{(n)} \cdot w_{i,j}{}^{(n)})$$

based on $\delta^{(n+1)}{}_j$, if the (n+1)-th layer is not the output layer, and $$\delta_j{}^{(n)} = (x_k{}^{(n+1)} - t_j{}^{(n+1)}) \cdot f'(\Sigma_i x_i{}^{(n)} \cdot w_{i,j}{}^{(n)})$$

if the (n+1)-th layer is the output layer 1330, wherein f' is the first derivative of the activation function, and $y^{(n+1)}{}_j$ is the comparison training value for the j-th node of the output layer 1330.

Figure 14:
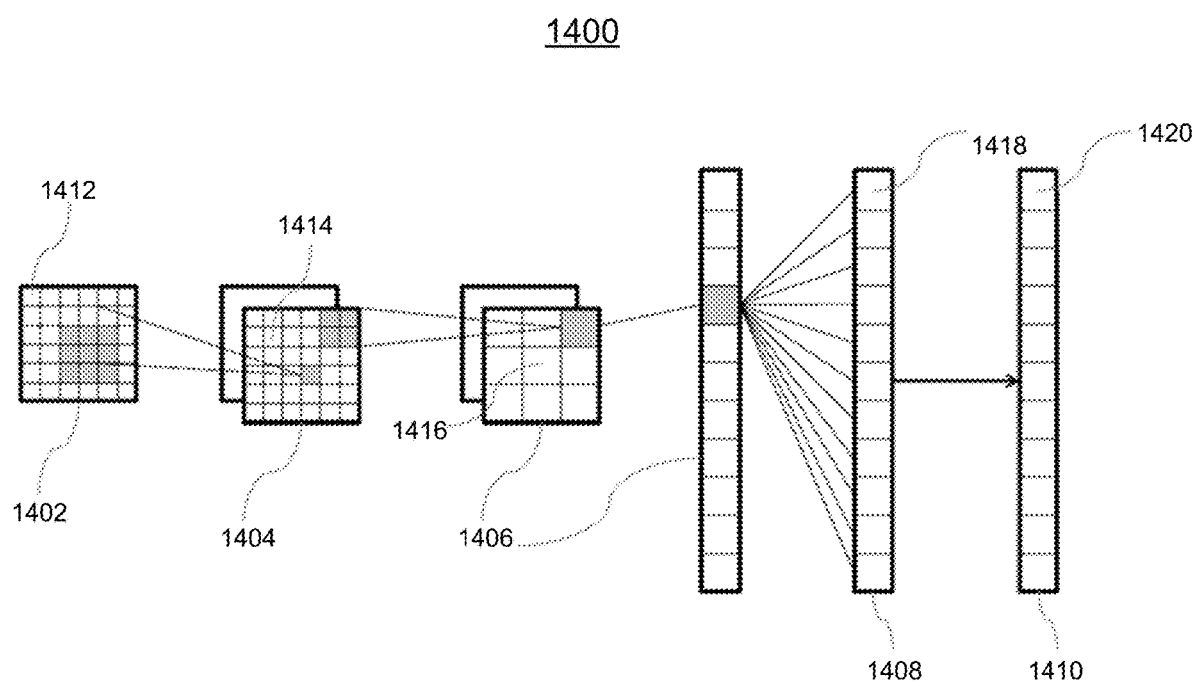
FIG. 14 shows a convolutional neural network that may be used to implement one or more embodiments.

FIG. 14 shows a convolutional neural network 1400, in accordance with one or more embodiments. Machine learning networks described herein, such as, e.g., the machine learning based networks utilized for implementing tumor-centered tools 302, anatomy-centered tools 304, text manipulation tools 306, and lymph node station identifier tools 308 of FIG. 3, may be implemented using convolutional neural network 1400.

In the embodiment shown in FIG. 14, the convolutional neural network comprises 1400 an input layer 1402, a convolutional layer 1404, a pooling layer 1406, a fully connected layer 1408, and an output layer 1410. Alternatively, the convolutional neural network 1400 can comprise several convolutional layers 1404, several pooling layers 1406, and several fully connected layers 1408, as well as other types of layers. The order of the layers can be chosen arbitrarily, usually fully connected layers 1408 are used as the last layers before the output layer 1410.

In particular, within a convolutional neural network 1400, the nodes 1412-1420 of one layer 1402-1410 can be considered to be arranged as a d-dimensional matrix or as a d-dimensional image. In particular, in the two-dimensional case the value of the node 1412-1420 indexed with i and j in the n-th layer 1402-1410 can be denoted as $x^{(n)}{}_{[i,j]}$. However, the arrangement of the nodes 1412-1420 of one layer 1402-1410 does not have an effect on the calculations executed within the convolutional neural network 1400 as such, since these are given solely by the structure and the weights of the edges.

In particular, a convolutional layer 1404 is characterized by the structure and the weights of the incoming edges forming a convolution operation based on a certain number of kernels. In particular, the structure and the weights of the incoming edges are chosen such that the values $x^{(n)}{}_k$ of the nodes 1414 of the convolutional layer 1404 are calculated as a convolution $x^{(n)}{}_k = (K_k * x^{(n-1)})$ based on the values $x^{(n-1)}$ of the nodes 1412 of the preceding layer 1402, where the convolution * is defined in the two-dimensional case as $$x_k{}^{(n)}[i,j] = (K_k * x^{(n-1)})[i,j] = \Sigma_{i'} \Sigma_{j'} K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 1412-1418 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 1412-1420 in the respective layer 1402-1410. In particular, for a convolutional layer 1404, the number of nodes 1414 in the convolutional layer is equivalent to the number of nodes 1412 in the preceding layer 1402 multiplied with the number of kernels.

If the nodes 1412 of the preceding layer 1402 are arranged as a d-dimensional matrix, using a plurality of kernels can be interpreted as adding a further dimension (denoted as "depth" dimension), so that the nodes 1414 of the convolutional layer 1404 are arranged as a (d+1)-dimensional matrix. If the nodes 1412 of the preceding layer 1402 are already arranged as a (d+1)-dimensional matrix comprising a depth dimension, using a plurality of kernels can be interpreted as expanding along the depth dimension, so that the nodes 1414 of the convolutional layer 1404 are arranged also as a (d+1)-dimensional matrix, wherein the size of the (d+1)-dimensional matrix with respect to the depth dimension is by a factor of the number of kernels larger than in the preceding layer 1402.

The advantage of using convolutional layers 1404 is that spatially local correlation of the input data can exploited by enforcing a local connectivity pattern between nodes of adjacent layers, in particular by each node being connected to only a small region of the nodes of the preceding layer.

In embodiment shown in FIG. 14, the input layer 1402 comprises 36 nodes 1412, arranged as a two-dimensional 6×6 matrix. The convolutional layer 1404 comprises 72 nodes 1414, arranged as two two-dimensional 6×6 matrices, each of the two matrices being the result of a convolution of the values of the input layer with a kernel. Equivalently, the nodes 1414 of the convolutional layer 1404 can be interpreted as arranges as a three-dimensional 6×6×2 matrix, wherein the last dimension is the depth dimension.

A pooling layer 1406 can be characterized by the structure and the weights of the incoming edges and the activation function of its nodes 1416 forming a pooling operation based on a non-linear pooling function f. For example, in the two dimensional case the values $x^{(n)}$ of the nodes 1416 of the pooling layer 1406 can be calculated based on the values $x^{(n-1)}$ of the nodes 1414 of the preceding layer 1404 as $$x^{(n)}[i,j] = f(x^{(n-1)}[id_1, jd_2], \ldots, x^{(n-1)}[id_1+d_1-1, id_2+d_2-1])$$

In other words, by using a pooling layer 1406, the number of nodes 1414, 1416 can be reduced, by replacing a number d1·d2 of neighboring nodes 1414 in the preceding layer 1404 with a single node 1416 being calculated as a function of the values of said number of neighboring nodes in the pooling layer. In particular, the pooling function f can be the max-function, the average or the L2-Norm. In particular, for a pooling layer 1406 the weights of the incoming edges are fixed and are not modified by training.

The advantage of using a pooling layer 1406 is that the number of nodes 1414, 1416 and the number of parameters is reduced. This leads to the amount of computation in the network being reduced and to a control of overfitting.

In the embodiment shown in FIG. 14, the pooling layer 1406 is a max-pooling, replacing four neighboring nodes with only one node, the value being the maximum of the values of the four neighboring nodes. The max-pooling is applied to each d-dimensional matrix of the previous layer;

in this embodiment, the max-pooling is applied to each of the two two-dimensional matrices, reducing the number of nodes from 72 to 18.

A fully-connected layer 1408 can be characterized by the fact that a majority, in particular, all edges between nodes 1416 of the previous layer 1406 and the nodes 1418 of the fully-connected layer 1408 are present, and wherein the weight of each of the edges can be adjusted individually.

In this embodiment, the nodes 1416 of the preceding layer 1406 of the fully-connected layer 1408 are displayed both as two-dimensional matrices, and additionally as non-related nodes (indicated as a line of nodes, wherein the number of nodes was reduced for a better presentability). In this embodiment, the number of nodes 1418 in the fully connected layer 1408 is equal to the number of nodes 1416 in the preceding layer 1406. Alternatively, the number of nodes 1416, 1418 can differ.

Furthermore, in this embodiment, the values of the nodes 1420 of the output layer 1410 are determined by applying the Softmax function onto the values of the nodes 1418 of the preceding layer 1408. By applying the Softmax function, the sum the values of all nodes 1420 of the output layer 1410 is 1, and all values of all nodes 1420 of the output layer are real numbers between 0 and 1.

A convolutional neural network 1400 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 1400 can be trained based on the backpropagation algorithm. For preventing overfitting, methods of regularization can be used, e.g. dropout of nodes 1412-1420, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-2, 4-8, and 10-11. Certain steps or functions of the methods and workflows described herein, including one or more of the steps or functions of FIGS. 1-2, 4-8, and 10-11, may be performed by a server or by another processor in a network-based cloud-computing system. Certain steps or functions of the methods and workflows described herein, including one or more of the steps of FIGS. 1-2, 4-8, and 10-11, may be performed by a client computer in a network-based cloud computing system. The steps or functions of the methods and workflows described herein, including one or more of the steps of FIGS. 1-2, 4-8, and 10-11, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-2, 4-8, and 10-11, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 15:
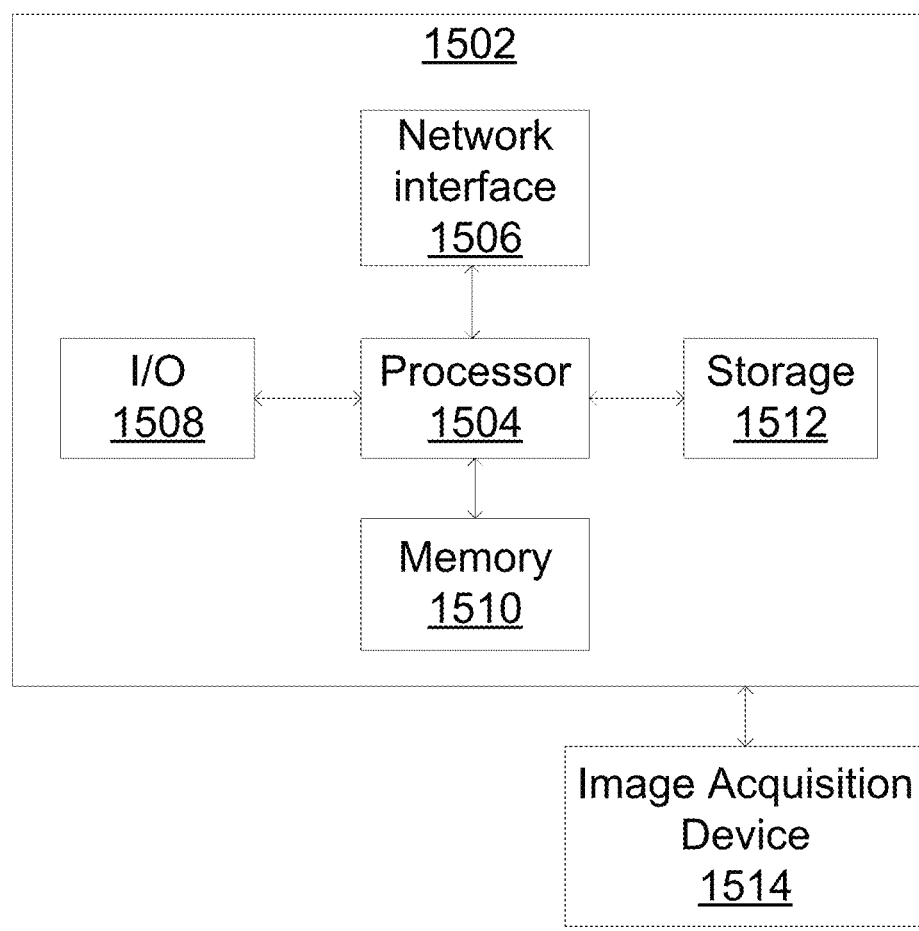
FIG. 15 shows a high-level block diagram of a computer that may be used to implement one or more embodiments.

A high-level block diagram of an example computer 1502 that may be used to implement systems, apparatus, and methods described herein is depicted in FIG. 15. Computer 1502 includes a processor 1504 operatively coupled to a data storage device 1512 and a memory 1510. Processor 1504 controls the overall operation of computer 1502 by executing computer program instructions that define such operations. The computer program instructions may be stored in data storage device 1512, or other computer readable medium, and loaded into memory 1510 when execution of the computer program instructions is desired. Thus, the method and workflow steps or functions of FIGS. 1-2, 4-8, and 10-11 can be defined by the computer program instructions stored in memory 1510 and/or data storage device 1512 and controlled by processor 1504 executing the computer program instructions. For example, the computer program instructions can be implemented as computer executable code programmed by one skilled in the art to perform the method and workflow steps or functions of FIGS. 1-2, 4-8, and 10-11. Accordingly, by executing the computer program instructions, the processor 1504 executes the method and workflow steps or functions of FIGS. 1-2, 4-8, and 10-11. Computer 1502 may also include one or more network interfaces 1506 for communicating with other devices via a network. Computer 1502 may also include one or more input/output devices 1508 that enable user interaction with computer 1502 (e.g., display, keyboard, mouse, speakers, buttons, etc.).

Processor 1504 may include both general and special purpose microprocessors, and may be the sole processor or one of multiple processors of computer 1502. Processor 1504 may include one or more central processing units (CPUs), for example. Processor 1504, data storage device 1512, and/or memory 1510 may include, be supplemented by, or incorporated in, one or more application-specific integrated circuits (ASICs) and/or one or more field programmable gate arrays (FPGAs).

Data storage device 1512 and memory 1510 each include a tangible non-transitory computer readable storage medium. Data storage device 1512, and memory 1510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1508 may include peripherals, such as a printer, scanner, display screen, etc. For example, input/output devices 1508 may include a display device such as a cathode ray tube (CRT) or liquid crystal display (LCD) monitor for displaying information to the user, a keyboard, and a pointing device such as a mouse or a trackball by which the user can provide input to computer 1502.

An image acquisition device 1514 can be connected to the computer 1502 to input image data (e.g., medical images) to the computer 1502. It is possible to implement the image acquisition device 1514 and the computer 1502 as one device. It is also possible that the image acquisition device 1514 and the computer 1502 communicate wirelessly through a network. In a possible embodiment, the computer 1502 can be located remotely with respect to the image acquisition device 1514.

Any or all of the systems and apparatus discussed herein may be implemented using one or more computers such as computer 1502.

One skilled in the art will recognize that an implementation of an actual computer or computer system may have other structures and may contain other components as well, and that FIG. 15 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:
1. A computer-implemented method comprising:
receiving patient data relating to a cancer of a patient, the patient data comprising one or more medical images and one or more biopsy reports;
determining a T-stage of the cancer based on a location and a size of one or more tumors of the cancer determined using the patient data;
determining an N-stage of the cancer by combining a metastasis evaluation of the cancer in regional lymph nodes determined from the one or more medical images and a metastasis evaluation of the cancer in the regional lymph nodes determined from the one or more biopsy reports;
determining an M-stage of the cancer based on a metastasis evaluation of the cancer in anatomical structures based on the patient data; and
outputting the T-stage, the N-stage, and the M-stage,
wherein at least one of the determining the T-stage, the determining of the N-stage, and the determining the M-stage is performed using one or more machine learning based networks.

2. The computer-implemented method of claim 1, wherein determining an N-stage of the cancer by combining a metastasis evaluation of the cancer in regional lymph nodes determined from the one or more medical images and a metastasis evaluation of the cancer in the regional lymph nodes determined from the one or more biopsy reports comprises:
comparing the metastasis evaluation of the cancer in the regional lymph nodes determined from the one or more medical images and the metastasis evaluation of the cancer in the regional lymph nodes determined from the one or more biopsy reports;
determining combined metastasis results based on the comparing; and
determining the N-stage of the cancer based on the combined metastasis results.

3. The computer-implemented method of claim 2, wherein comparing the metastasis evaluation of the cancer in the regional lymph nodes determined from the one or more medical images and the metastasis evaluation of the cancer in the regional lymph nodes determined from the one or more biopsy reports comprises:
comparing the metastasis evaluation of the cancer in the regional lymph nodes determined from the one or more medical images and the metastasis evaluation of the cancer in the regional lymph nodes determined from the one or more biopsy reports based on a level of evidence,
where the level of evidence comprises 1) a first level of evidence comprising a positive biopsy result, 2) a second level of evidence comprising negative metastasis regions determined from the one or more medical images, 3) a third level of evidence comprising a negative biopsy result, and 4) a fourth level of evidence comprising positive metastasis regions determined from the one or more medical images.

4. The computer-implemented method of claim 1, wherein determining a T-stage of the cancer based on a location and a size of one or more tumors of the cancer determined using the patient data comprises:
- determining the one or more tumors to be located in an area around a phrenic nerve in response to a diaphragm of the patient being at least partially paralyzed; and
- determining the T-stage of the cancer based on the determination that the one or more tumors are located in the area around the phrenic nerve.

5. The computer-implemented method of claim 1, further comprising:
- determining whether a detection and a malignancy classification of the one or more tumors determined from the one or more medical images conform to the one or more biopsy reports.

6. The computer-implemented method of claim 1, wherein outputting the T-stage, the N-stage, and the M-stage comprises:
- presenting a path taken along a series of decisions for the determining the T-stage, the determining the N-stage, and the determining the M-stage.

7. The computer-implemented method of claim 1, further comprising:
- presenting the one or more medical images annotated with anatomies, measurements, and findings determined using the one or more machine learning based networks.

8. The computer-implemented method of claim 1, where the cancer is a non-small cell lung cancer.

9. An apparatus comprising:
- means for receiving patient data relating to a cancer of a patient, the patient data comprising one or more medical images and one or more biopsy reports;
- means for determining a T-stage of the cancer based on a location and a size of one or more tumors of the cancer determined using the patient data;
- means for determining an N-stage of the cancer by combining a metastasis evaluation of the cancer in regional lymph nodes determined from the one or more medical images and a metastasis evaluation of the cancer in the regional lymph nodes determined from the one or more biopsy reports;
- means for determining an M-stage of the cancer based on a metastasis evaluation of the cancer in anatomical structures based on the patient data; and
- means for outputting the T-stage, the N-stage, and the M-stage,
- wherein at least one of the means for determining the T-stage, the means for determining of the N-stage, and the means for determining the M-stage is performed using one or more machine learning based networks.

10. The apparatus of claim 9, wherein the means for determining an N-stage of the cancer by combining a metastasis evaluation of the cancer in regional lymph nodes determined from the one or more medical images and a metastasis evaluation of the cancer in the regional lymph nodes determined from the one or more biopsy reports comprises:
- means for comparing the metastasis evaluation of the cancer in the regional lymph nodes determined from the one or more medical images and the metastasis evaluation of the cancer in the regional lymph nodes determined from the one or more biopsy reports;
- means for determining combined metastasis results based on the comparing; and
- means for determining the N-stage of the cancer based on the combined metastasis results.

11. The apparatus of claim 10, wherein the means for comparing the metastasis evaluation of the cancer in the regional lymph nodes determined from the one or more medical images and the metastasis evaluation of the cancer in the regional lymph nodes determined from the one or more biopsy reports comprises:
- means for comparing the metastasis evaluation of the cancer in the regional lymph nodes determined from the one or more medical images and the metastasis evaluation of the cancer in the regional lymph nodes determined from the one or more biopsy reports based on a level of evidence,
- where the level of evidence comprises 1) a first level of evidence comprising a positive biopsy result, 2) a second level of evidence comprising negative metastasis regions determined from the one or more medical images, 3) a third level of evidence comprising a negative biopsy result, and 4) a fourth level of evidence comprising positive metastasis regions determined from the one or more medical images.

12. The apparatus of claim 9, wherein the means for determining a T-stage of the cancer based on a location and a size of one or more tumors of the cancer determined using the patient data comprises:
- means for determining the one or more tumors to be located in an area around a phrenic nerve in response to a diaphragm of the patient being at least partially paralyzed; and
- means for determining the T-stage of the cancer based on the determination that the one or more tumors are located in the area around the phrenic nerve.

13. The apparatus of claim 9, further comprising:
- means for determining whether a detection and a malignancy classification of the one or more tumors determined from the one or more medical images conform to the one or more biopsy reports.

14. The apparatus of claim 9, wherein the means for outputting the T-stage, the N-stage, and the M-stage comprises:
- means for presenting a path taken along a series of decisions for the determining the T-stage, the determining the N-stage, and the determining the M-stage.

15. A non-transitory computer readable medium storing computer program instructions, the computer program instructions when executed by a processor cause the processor to perform operations comprising:
- receiving patient data relating to a cancer of a patient, the patient data comprising one or more medical images and one or more biopsy reports;
- determining a T-stage of the cancer based on a location and a size of one or more tumors of the cancer determined using the patient data;
- determining an N-stage of the cancer by combining a metastasis evaluation of the cancer in regional lymph nodes determined from the one or more medical images and a metastasis evaluation of the cancer in the regional lymph nodes determined from the one or more biopsy reports;
- determining an M-stage of the cancer based on a metastasis evaluation of the cancer in anatomical structures based on the patient data; and outputting the T-stage, the N-stage, and the M-stage,
wherein at least one of the determining the T-stage, the determining of the N-stage, and the determining the M-stage is performed using one or more machine learning based networks.

16. The non-transitory computer readable medium of claim 15, wherein determining an N-stage of the cancer by combining a metastasis evaluation of the cancer in regional lymph nodes determined from the one or more medical images and a metastasis evaluation of the cancer in the regional lymph nodes determined from the one or more biopsy reports comprises:
comparing the metastasis evaluation of the cancer in the regional lymph nodes determined from the one or more medical images and the metastasis evaluation of the cancer in the regional lymph nodes determined from the one or more biopsy reports;
determining combined metastasis results based on the comparing; and
determining the N-stage of the cancer based on the combined metastasis results.

17. The non-transitory computer readable medium of claim 16, wherein comparing the metastasis evaluation of the cancer in the lymph nodes determined from the one or more medical images and the metastasis evaluation of the cancer in the lymph nodes determined from the one or more biopsy reports comprises:
comparing the metastasis evaluation of the cancer in the lymph nodes determined from the one or more medical images and the metastasis evaluation of the cancer in the lymph nodes determined from the one or more biopsy reports based on a level of evidence,
where the level of evidence comprises 1) a first level of evidence comprising a positive biopsy result, 2) a second level of evidence comprising negative metastasis regions determined from the one or more medical images, 3) a third level of evidence comprising a negative biopsy result, and 4) a fourth level of evidence comprising positive metastasis regions determined from the one or more medical images.

18. The non-transitory computer readable medium of claim 15, wherein determining a T-stage of the cancer based on a location and a size of one or more tumors of the cancer determined using the patient data comprises:
determining the one or more tumors to be located in an area around a phrenic nerve in response to a diaphragm of the patient being at least partially paralyzed; and
determining the T-stage of the cancer based on the determination that the one or more tumors are located in the area around the phrenic nerve.

19. The non-transitory computer readable medium of claim 15, further comprising:
presenting the one or more medical images annotated with anatomies, measurements, and findings determined using the one or more machine learning based networks.

20. The non-transitory computer readable medium of claim 15, where the cancer is a non-small cell lung cancer.

* * * * *